(12) United States Patent
Wright

(10) Patent No.: US 7,267,680 B2
(45) Date of Patent: Sep. 11, 2007

(54) ANASTOMOSIS APPARATUS AND METHODS OF DEPLOYMENT AND MANUFACTURE

(76) Inventor: David Walter Wright, 5 Willowleaf Dr., Littleton, CO (US) 80127

( * ) Notice: Subject to any disclaimer, the term of this patent is extended or adjusted under 35 U.S.C. 154(b) by 432 days.

(21) Appl. No.: 10/683,257

(22) Filed: Oct. 8, 2003

(65) Prior Publication Data

US 2005/0080437 A1    Apr. 14, 2005

(51) Int. Cl.
*A61B 17/08* (2006.01)

(52) U.S. Cl. ...................... 606/153; 606/151

(58) Field of Classification Search ............ 606/153, 606/139, 155, 148, 151, 213; 623/1.14, 1.36, 623/1.13, 1.11
See application file for complete search history.

(56) References Cited

U.S. PATENT DOCUMENTS

| | | | | |
|---|---|---|---|---|
| 5,234,447 A | * | 8/1993 | Kaster et al. | 606/153 |
| 5,904,697 A | * | 5/1999 | Gifford et al. | 606/155 |
| 6,152,937 A | * | 11/2000 | Peterson et al. | 606/153 |
| 6,235,045 B1 | * | 5/2001 | Barbut et al. | 606/200 |
| 6,440,163 B1 | | 8/2002 | Swanson et al. | |
| 6,494,889 B1 | | 12/2002 | Fleischman et al. | |
| 6,508,822 B1 | | 1/2003 | Peterson et al. | |
| 6,659,327 B2 | * | 12/2003 | Heck et al. | 227/175.1 |
| 6,966,917 B1 | * | 11/2005 | Suyker et al. | 606/148 |
| 2004/0092960 A1 | * | 5/2004 | Abrams et al. | 606/139 |
| 2004/0217146 A1 | * | 11/2004 | Beck | 227/176.1 |

OTHER PUBLICATIONS

St. Jude Medical Reshaping the Future, Symmetry Bypass System—Aortic Connector, 2000 St. Paul, Minnesota, USA.

* cited by examiner

*Primary Examiner*—Anhtuan T. Nguyen
*Assistant Examiner*—Natalie Pous

(57) ABSTRACT

A method and apparatus for making an anastomosis between a tubular duct and a vessel has an annulus having a longitudinal axis, a first set of fingers and a second set of fingers. The first set of fingers extend axially from the annulus in one direction and the second set of fingers extending axially from the annulus in another direction generally opposite the direction of the first set of fingers. The first and second sets of fingers are movable to penetrate the tubular duct and the vessel, respectively, as they move from a biased configuration to an unbiased configuration.

41 Claims, 20 Drawing Sheets

ANASTOMOSIS APPARATUS AND METHODS OF DEPLOYMENT AND MANUFACTURE

BACKGROUND OF THE INVENTION

1. Field of the Invention

This invention relates generally to methods and devices for surgically joining separate pieces of tissue to one another, and more particularly to surgically joining a tubular graft of tissue to a separate piece of tissue.

2. Related Art

In performing bypass surgery, it is a known practice to repair clogged or an otherwise damaged segment of tubular tissue, for example an artery, by cultivating a healthy section of artery from a remote location of the body, for example, a thigh, and replacing the damaged section with the cultivated section of artery. In addition, it is also known to bypass a clogged or damaged section of artery by rerouting a healthy section of the artery with the cultivated segment of artery attached thereto, and then attaching an end of the cultivated section of artery to another piece of tissue, for example, a wall of a heart.

While performing the procedures mentioned above, a surgeon must ordinarily spend an exhaustive amount of time completing the procedures, generally ranging between 2 to 6 hours or more. Much of the surgeon's time is spent making certain that the segments of tissue are joined together in a leak-proof anastomosis. Generally, this requires the surgeon to make numerous stitches of suture between the segments of tissue being joined to one another, and in some cases replacing sutures that do not create a leak-proof anastomosis between the pieces of tissue.

Though using sutures to join segments of tissue to one another in open heart surgery, or other forms of surgery, has proven successful, not only does it require an exhaustive amount of time in surgery, there is also a danger of the suture becoming damaged. Damage to a portion of the suture may result in many ways, such as through inadvertent grasping or clamping by a surgical instrument. Ordinarily, a damaged piece of suture has a substantially reduced tensile strength and thus may ultimately fail to maintain the pieces of tissue joined to one another.

SUMMARY OF THE INVENTION

An apparatus for making an anastomosis between a tubular duct and a wall of a vessel has an annulus with a longitudinal axis, a first set of fingers and a second set of fingers. The first set of fingers extend axially from the annulus in one direction and are movable between a biased, linear configuration and a unbiased, arcuate configuration extending generally radially inwardly toward the longitudinal axis. The second set of fingers extending axially from the annulus in another direction generally opposite the direction of the first set of fingers. The second set of fingers are movable between a biased, linear configuration and a unbiased, arcuate configuration extending generally radially outwardly from the longitudinal axis. The first set of fingers are configured to penetrate the wall of the tubular duct as they move from their biased configuration to their unbiased configuration, while the second set of fingers are configured to penetrate the wall of the vessel as they move from their biased configuration to their unbiased configuration.

Another aspect of this invention includes a method of manufacture of an apparatus providing an anastomosis between a tubular duct and a wall of a vessel. The steps include providing a thin sheet of material and fabricating a generally flat annular pattern from the sheet. The pattern is fabricated having a first set of fingers extending radially inwardly toward one another and a second set of fingers extending radially outwardly away from one another. A further step includes providing a mandrel having an outer surface and forming the pattern to conform to the outer surface of the mandrel. A further step includes providing a heat source and applying heat from the heat source to the pattern to maintain said pattern in resilient conformity with the outer surface of said mandrel to maintain the first and second sets of fingers in a unbiased, arcuate configuration.

Another aspect of this invention provides an apparatus for deploying a fastener to attach a tubular duct to a wall of a vessel. The apparatus has a housing having an inner wall defining a generally cylindrical passage. The apparatus further includes a generally cylindrical plunger sized for receipt in the cylindrical passage of the housing. Additionally, the apparatus has a mandrel having a generally cylindrical outer surface projecting axially sufficiently to bear against a first and second set of fingers of the fastener. The outer surface of the mandrel is sized to accommodate the fastener and the plunger between the outer surface and said passage of said housing.

Objects, features and advantages of this invention include an apparatus and method that provide a secure and reliable anastomosis between a tubular duct and a wall of a vessel, establish a quick biocompatible bond between mating tissues, impart a biasing force maintaining mating tissues in abutting contact with one another, readily penetrates tissue without damaging the tissue, provides a quick and reliable mechanism in which to attach separate tissues to one another, is of relatively simple design and is economical in manufacture, use and assembly.

BRIEF DESCRIPTION OF THE DRAWINGS

These and other objects, features and advantages of this invention will become apparent from the following detailed description of the preferred embodiments and best mode, appended claims and accompanying drawings in which:

DETAILED DESCRIPTION OF THE PREFERRED EMBODIMENTS

Figure 1:
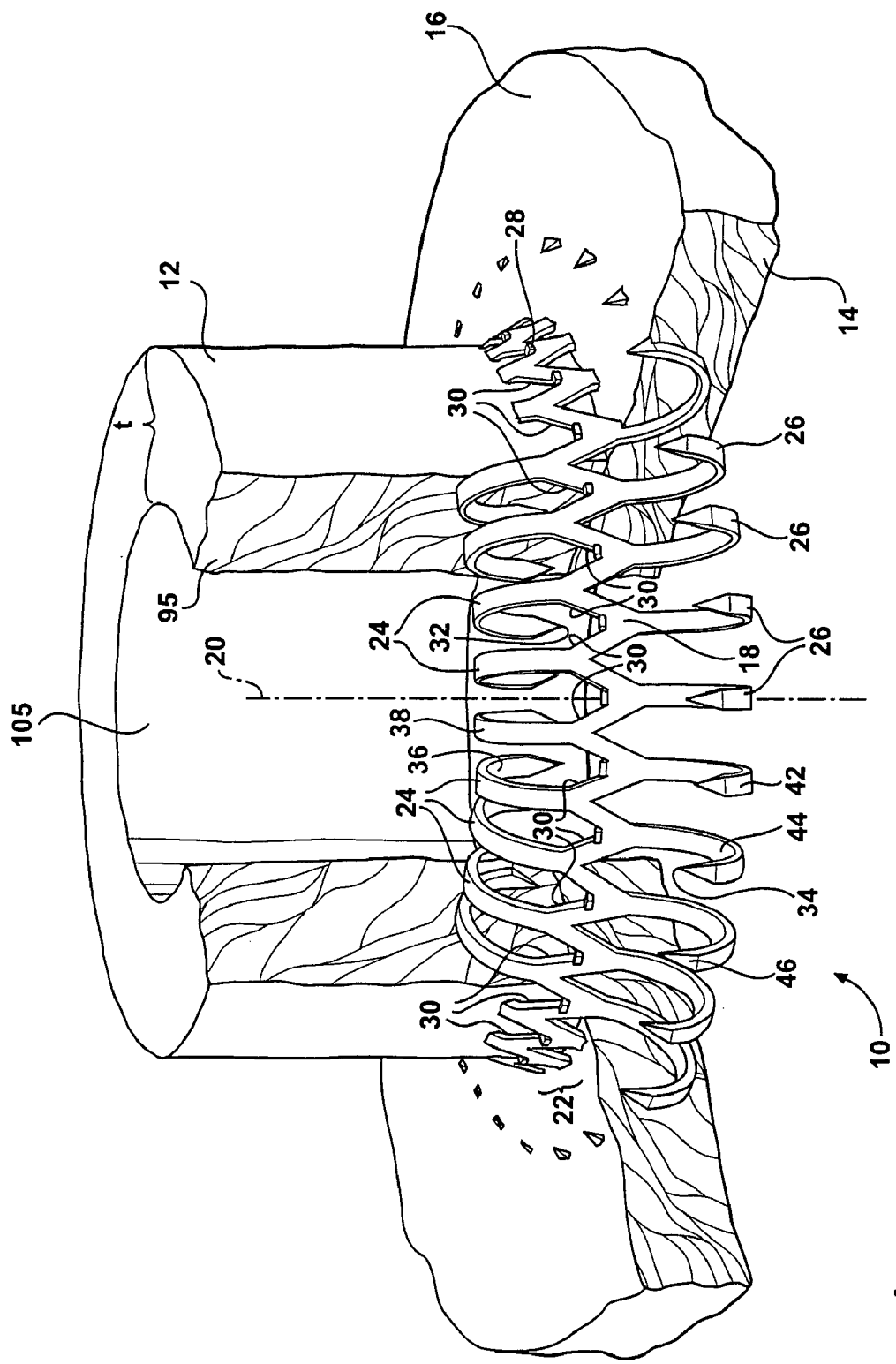
FIG. 1 is a perspective view with a portion cut away illustrating an apparatus constructed according to one presently preferred embodiment of the invention joining a tubular duct to a wall of a vessel.

Referring to FIG. 1, an apparatus, referred to hereafter as a fastener 10, is shown making an anastomosis between two pieces of tissue, represented here as a wall 11 of a generally tubular duct 12, for example and without limitation, a graft of an artery, and a wall 14 of a vessel 16, for example and without limitation, a heart wall. The anastomosis established by the fastener 10 provides a sutureless connection between the tubular duct 12 and the vessel 16. Desirably, the fastener 10 biases the tubular duct 12 and the wall 14 of the vessel 16 toward one another, thereby establishing a leak-proof connection between the tubular duct 12 and the vessel 16. Additionally, the continual bias of the tubular duct 12 against the wall 14 of the vessel 16 facilitates the formation of a biological bond between the tubular duct 12 and the vessel 16.

Still referring to FIG. 1, the fastener 10 has an annulus 18 with a longitudinal axis 20. The annulus 18 has a generally accordion shaped, "zig-zag", sinusoidal or serpentine shaped midsection 22 extending annularly between a first set of fingers 24 and a second set of fingers 26. The "zig-zag" shape facilitates the ability of the fastener 10 to take on its final form in manufacture by distributing the stresses over an expanded area from that of a cylindrical form. The It should be recognized that the midsection 22 may be constructed having other shapes than the "zig-zag" shape, may be either symmetrical or asymmetrical, and otherwise could be formed as a solid annular band of material.

Preferably, the annulus 18 has a plurality of tangs 28 to facilitate joining the fastener 10 to at least one of the tubular duct 12 and vessel 16. While in an unbiased state, the tangs 28 extend radially outwardly from the midsection 22, shown here as extending radially from each of a plurality of valleys 30 established by the midsection 22. It should be recognized that the tangs 28 may be formed to extend from selected valleys 30, as desired for the intended application. Also, the tangs 28 may be formed to extend from other locations on the annulus 18 than the valleys 30, as desired.

Figure 3:
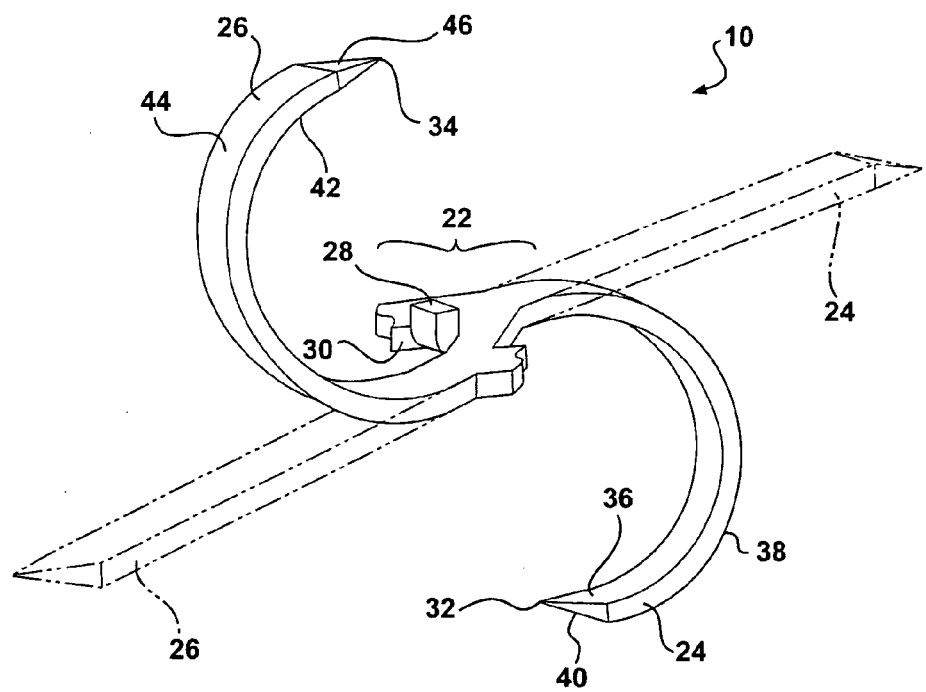
FIG. 3 is a partial perspective view of the apparatus shown in a preformed state and in a formed state.
Figure 6A:
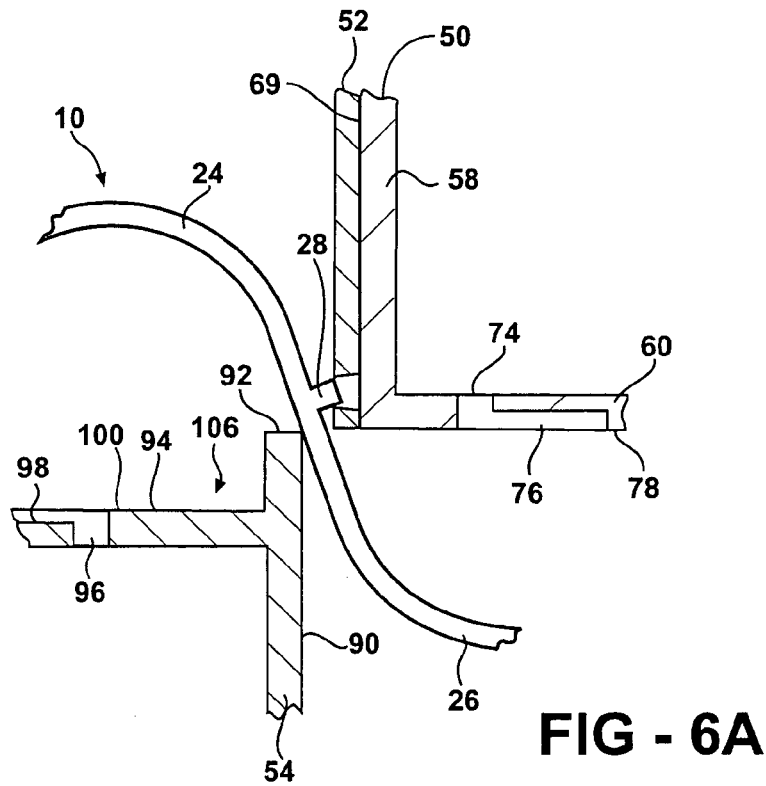
FIGS. 6A and 7A are partially enlarged views of the apparatus being received in a portion of the plunger.
Figure 6:
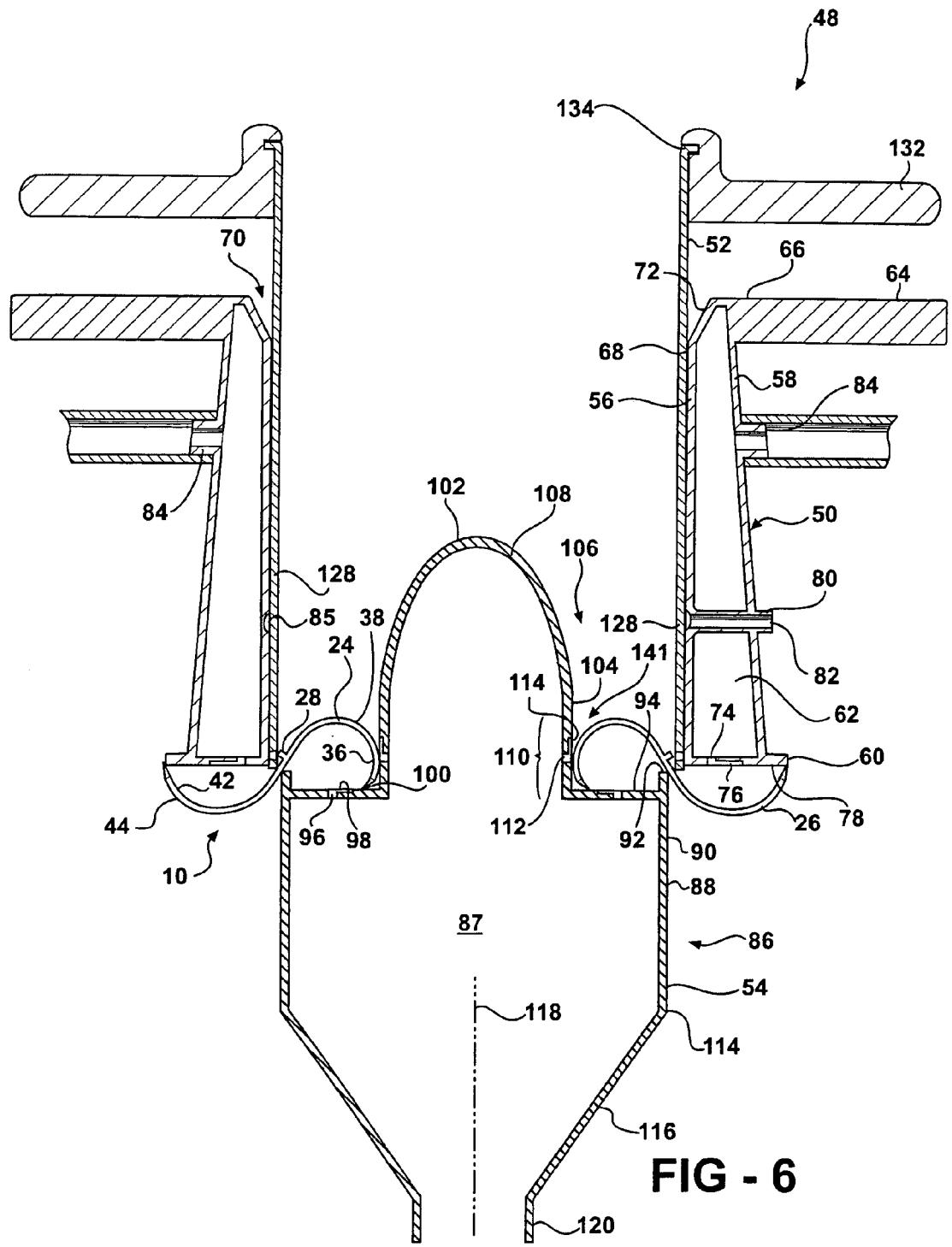
FIGS. 6-8 are cross-sectional views of a mandrel loading the apparatus into the housing and plunger.

In the final manufactured form, the first set of fingers 24 extend generally axially from the annulus 18 in one direction to a 180 degree bend extending generally radially inwardly toward the longitudinal axis 20, thereafter, leading to free ends 32. The second set of fingers 26 extend generally axially from the annulus 18 in another direction generally opposite the direction of the first set of fingers 24 to a 180 degree bend extending generally radially outwardly from the longitudinal axis 20, thereafter, leading to free ends 34. The midsection 22 generally remains generally cylindrical in form, while the bends in the respective sets of fingers 24, 26, define the generally arcuate, or curved portions of the fastener 10 that define a generally S-shaped fastener in axial cross-section, as best shown in FIGS. 1, 3 and 6. It should be recognized that the fingers 24, 26, and midsection 22 may be formed having different geometries than described above, for example, the fingers 24, 26 may have a plurality of stepped linear sections defining the generally hook shaped configuration and the midsection 22 may be formed having an arcuate configuration.

The first set of fingers 24 are moveable or bendable between a first, extended or biased, generally linear or at least partially flattened configuration and a second, retracted or unbiased, at least partially arcuate, hook shaped, curled or otherwise nonlinear configuration extending at least in part generally radially inwardly toward the longitudinal axis 20 to penetrate the tubular duct 12 in use. The second set of fingers 26 are moveable or bendable between a first, extended or biased, generally linear or at least partially flattened configuration and a second, retracted or unbiased, at least partially arcuate, hook shaped, curled or otherwise nonlinear configuration extending at least in part generally radially outwardly from the longitudinal axis 20 to penetrate the wall 14 of the vessel 16 in use.

The first set of fingers 24 have an inner surface 36 and an outer surface 38 terminating at the free ends 32 that preferably define a point to facilitating piercing a piece of tissue, such as the tubular duct 12 and vessel 16, for example. When the first set of fingers 24 are in their biased and generally flattened configuration (FIG. 8), the outer surfaces 38 face generally away from the longitudinal axis 20 and the inner surface 36 face generally toward the longitudinal axis 20. Desirably, the first set of fingers 24 each have a bevel 40, such that when in their biased configuration, the bevels 40 extend from each free end 32 along at least a portion of the outer surfaces 38 and generally away from the longitudinal axis 20.

The second set of fingers 26 have an inner surface 42 and an outer surface 44 terminating at the free ends 34 that preferably define a point to facilitating piercing a piece of tissue, such as the tubular duct 12 and vessel 16, for example. When the second set of fingers 26 are in their biased configuration (FIG. 8), the inner surfaces 42 face generally toward the longitudinal axis 20 and the outer surfaces 44 face generally away from the longitudinal axis 20. Desirably, the second set of fingers 26 each have a bevel 46 extending from the free ends 34 along at least a portion of the inner surfaces 42 and generally toward the longitudinal axis 20.

The first and second sets of fingers 24, 26 are generally constructed in a staggered relation to each other such that they are circumferentially offset from one another. The fingers 24, 26 are constructed of a resiliently springy material so that they automatically return toward their unbiased, generally arcuate or hook shaped configuration when the force displacing or extending the fingers 24, 26 to their biased position is removed. Desirably, shape memory alloys are used in constructing the fastener 10, thereby giving the first and second sets of fingers 24, 26 their resiliently springy properties. Some exemplary materials include, without limitation, nitinol, MP35N, tantalum, tungsten, platinum, 304 stainless steel, and other stainless steels, as desired for the intended application.

The fastener 10 is desirably fabricated from a thin, flat sheet of material, for example, from one of the materials listed above. The thickness of the material used to construct the fastener 10 depends greatly on the elastic properties of the material. Desirably, when the fingers 24, 26 are in their biased, first positions, the material chosen remains in an elastic state of deformation, thereby allowing the fingers 24, 26 to return to their second, unbiased positions. If one of the materials listed above is used, a thickness of about 0.0001"-

Figure 2:
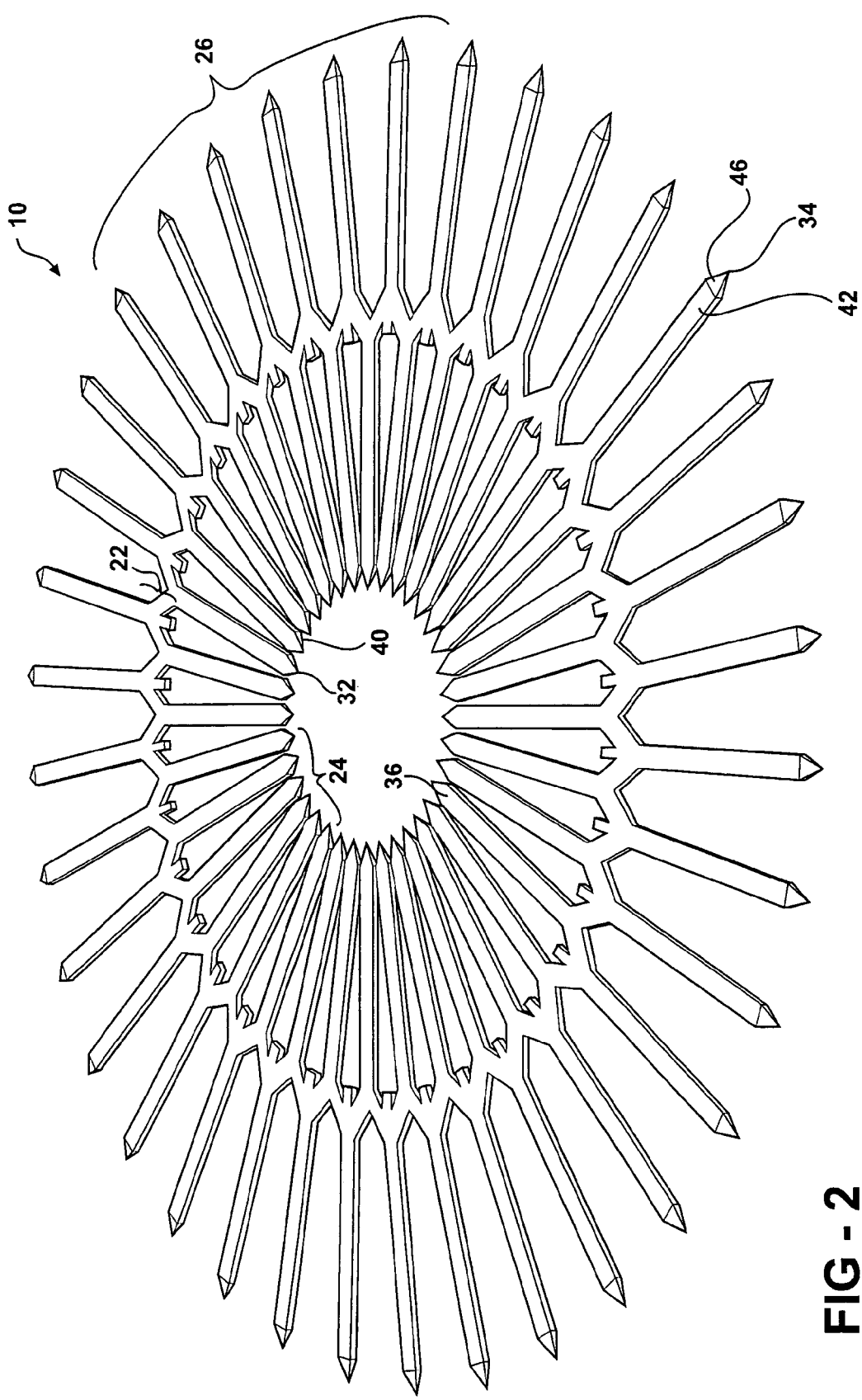
FIG. 2 is a perspective view of the apparatus of FIG. 1 in a preformed state of construction.

0.0150" is generally used, though it should be understood that the ultimate thickness may vary according to the material used. As best shown in FIG. 2, a generally flat annular pattern is constructed from the sheet, wherein the pattern has the first set of fingers 24 extending radially inwardly toward one another, while the second set of fingers 26 extend radially outwardly away from one another. The tangs 28 are shown between each of the first set of fingers 24 and extending in the same general direction as the first set of fingers 24. The method of manufacture may incorporate a variety of construction methods, for example and without limitation, photo-chemical etching, laser cutting, die punching, electric discharge machining (EDM), and other methods of construction, as desired. It should be understood that the first and second sets of fingers 24, 26 may be constructed having different lengths from one another, or the fingers within each separate set of finger 24, 26 may have different lengths from one another (not shown). By incorporating different lengths for the fingers within at least one of the first and second sets of fingers, 24, 26, the fingers 24, 26 may be attached and extend into to a piece of tissue oriented at an oblique angle relative to the longitudinal axis 20 of the fastener 10. This is of particular importance when making an end-side anastomosis where the two pieces of tissue being joined are often at oblique angles to one another.

To facilitate bonding between tissue and the fastener 10, both sides of the flat annual pattern, particularly the inner surfaces 36, 42 and the outer surfaces 38, 44 are preferably provided with a surface texture or roughed generally having a surface finish of about 30-60 RMS using a process such as chemical etching, or mead-blasting, for example. By creating a roughed surface, the tissue is better able to bond to the fastener 10.

Figure 2A:
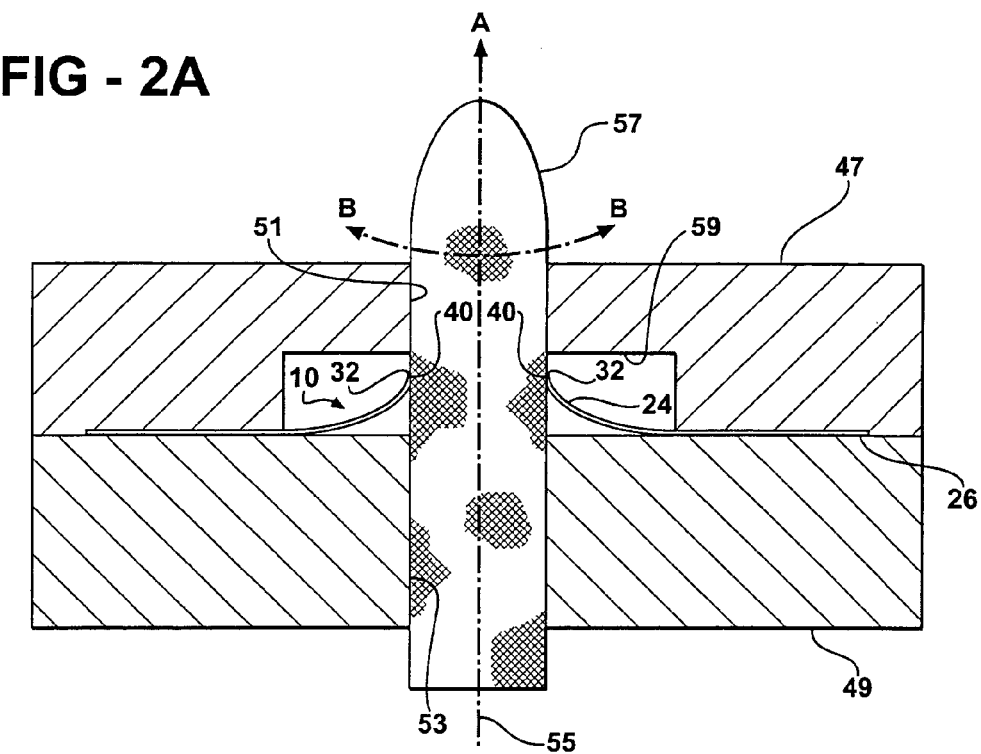
FIG. 2A is a cross-sectional view of the apparatus maintained between a pair of plates with a sharpening tool forming bevels on a first set of fingers of the apparatus.

As shown in FIG. 2A, desirably, while the fastener 10 is in its initially constructed flat configuration, the bevels 40 are formed on the first set of fingers 24. While forming the bevels 40 on the first set of fingers 24, the flat annual pattern is placed between a pair of generally flat dies or plates 47, 49. Each plate 47, 49 has a through hole 51, 53, respectively, sized to allow the first set of fingers 24 to extend radially inwardly of the through holes 51, 53 upon concentrically aligning the through holes 51, 53 and the first set of fingers 24 with one another along an axis 55. The plate 47 has a counter bore 59 to allow the first set of fingers 24 to deflect during the formation of the bevels 40.

In forming the bevels 40 on the first set of fingers 24, the fastener 10 is maintained between the plates 47, 49 so that a sharpening tool, for example and without limitation, a honing rod 57, can be passed in one direction, represented by arrow A, through the through holes 51, 53 of the plates 47, 49 to engage the free ends 32 of the first set of fingers 24. Accordingly, as the honing rod 57 engages the first set of fingers 24, the fingers deflect generally in the direction of arrow A, into the counter bore 59. As such, material is removed from the first set of fingers 24 to form the bevels 40. It should be recognized that the honing rod 57, in addition to being passed axially through the through holes 51, 53 of the plates 47, 49, can be rotated about the axis 55 in the direction of arrows B to facilitate forming a uniform bevel 40 on each of the first set of fingers 24.

Figure 2B:
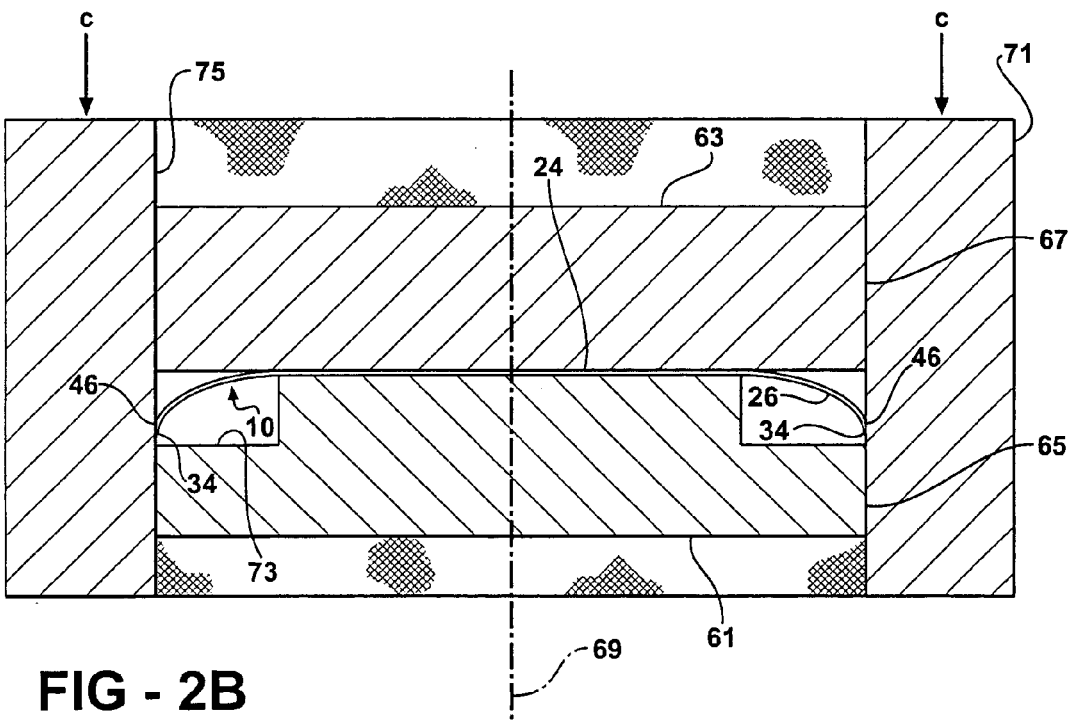
FIG. 2B is a cross-sectional view of the apparatus maintained in its between another pair of plates with a sharpening tool forming bevels on a second set of fingers of the apparatus.

As shown in FIG. 2B, desirably, while the fastener 10 is in its initially constructed flat configuration, the bevels 46 are formed on the second set of fingers 26. While forming the bevels 46 on the second set of fingers 26, the flat annual pattern is placed between a pair of generally flat dies or plates 61, 63. Each plate 61, 63 has a an outer diameter 65, 67, respectively, sized to allow the second set of fingers 26 to extend radially outwardly therefrom upon concentrically aligning the outer diameters 65, 67 and the second set of fingers 26 with one another along an axis 69, with the fastener 10 maintained between the plates 61, 63. The plate 61 has a recessed surface 73 to allow the second set of fingers 26 to deflect during the formation of the bevels 46.

In forming the bevels 46 on the second set of fingers 26, the fastener 10 is maintained between the plates 61, 63 so that a sharpening tool, for example and without limitation, a honing cylinder 71, can be passed in one direction, represented by arrows C, generally opposite to the direction of arrow A in which the honing rod 57 is passed, to engage the free ends 34 of the second set of fingers 26. The honing cylinder 71 has a bore 75 greater in diameter than the outer diameters 65, 67 of the plates 61, 63 and less than the outer diameter of the second set of fingers 26. Accordingly, as the honing cylinder 71 passes over the second set of fingers 26, the bore 75 engages the free ends 34 of the second set of fingers 26 and the fingers 26 deflect generally in the direction of arrow C, toward the recessed surface 73. As such, material is removed from the second set of fingers 26 and the bevels 46 are formed.

Figure 2C:
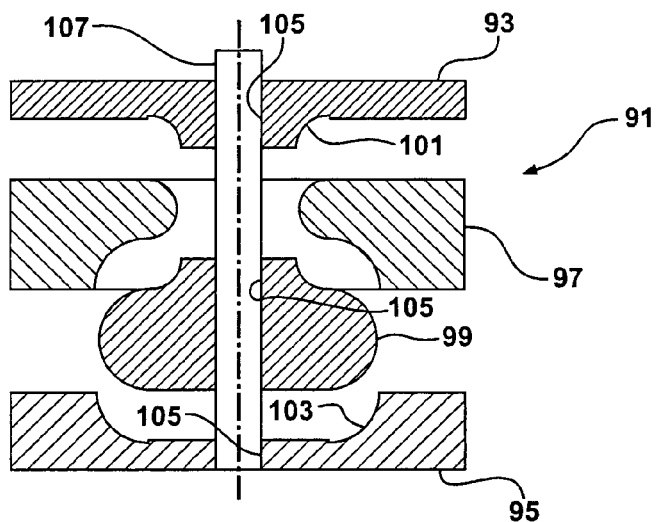
FIG. 2C is an exploded cross-sectional view of a set of dies for forming the apparatus.
Figure 2D:
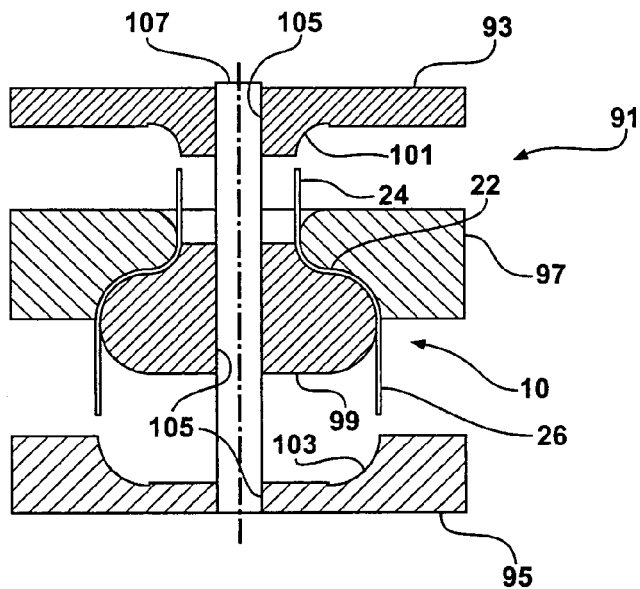
FIG. 2D is a cross-sectional view of the apparatus partially formed between a pair of the dies of FIG. 2C.
Figure 2E:
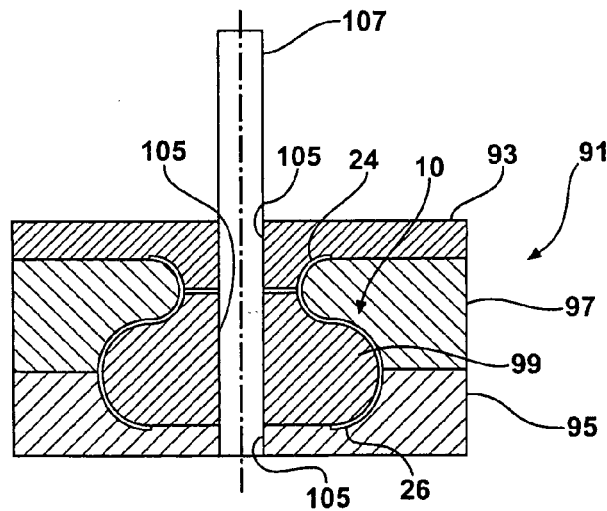
FIG. 2E is a cross-sectional view of the apparatus completely formed between the dies of FIG. 2C.

The flat annular pattern, as shown in FIG. 2, is then elastically deformed between a set of mating dies 91 (FIG. 2C) having mating contoured surfaces. The contoured surfaces of the dies 91 are constructed having a geometry suitable to provide the finished, unbiased shaped of the fastener 10, as best shown in FIGS. 1 and 3. The set of dies 91 is represented here having an upper die 93, a lower die 95, and a pair of intermediate dies 97, 99. As shown in FIG. 2D, the flat annular pattern is initially positioned between the intermediate dies 97, 99. The intermediate dies 95, 99 are then brought together to generally form the midsection 22 of the fastener 10. As shown in FIG. 2E, the upper and lower dies 93, 95 are then brought into contact with the intermediate dies 97, 99 to form the first and second sets of fingers 24, 26, respectively. Desirably, the upper and lower dies 93, 95 have recessed annular portions 101, 103, respectively, to accommodate receiving the first and second sets of fingers 24, 26. Further, to facilitate bringing the dies 91 together in a properly aligned fashion, the dies 91, other than the die 97, have through holes 105 sized to receive a guide rod 107 when concentrically aligned with one another.

The deformed pattern is maintained in conformity with the contoured surfaces of the dies 91 by subjecting the elastically deformed pattern to a controlled heat treatment process. During the heat treatment process, the deformed pattern is raised to the critical temperature of the material, for example, about 932° F. for nitinol, between about 800-1200° F. for MP35N, and is then quenched, preferably in water, to retain the pattern in conformity with the outer surfaces of the dies. Upon finishing the heat treatment process, the first set of fingers 24 are shaped to their unbiased, generally arcuate configuration extending at least partially generally radially inwardly toward the longitudinal axis 20, while the second set of fingers 26 are shaped to their unbiased, generally arcuate configuration extending at least partially generally radially outwardly from the longitudinal axis 20. Additionally, the tangs 28 are formed to take on an unbiased configuration extending radially outwardly from the midsection 22 and generally transversely to the longitudinal axis 20. It should be recognized that the dies 91 are constructed from a high temperature tool steel allowing them to be subjected to the heat treatment process without detriment to the dies 91.

Accordingly, the fastener 10 begins as a generally flat piece of material, and is transformed into the seamless annulus 18 having the arcuate first and second sets of fingers 24, 26 extending from the midsection 22 without the necessity of secondary welding or other types of bonding processes to create the generally cylindrical fastener 10. The generally serpentine or accordion configuration of the midsection 22 with the offset orientation of the fingers 24, 26 provides the resiliently springy material with the ability to flex and bend and essentially unfold in an accordion-like fashion from the generally flat piece of material, as shown in FIG. 2, to the generally cylindrical configuration of the fastener 10, as best shown in FIGS. 1 and 3. As a result, manufacturing efficiencies and reduced costs are attained by eliminating secondary manufacturing operations, for example, welding, or other bonding processes typically used to create a generally cylindrical fastener from a generally flat sheet of material. It should be recognized that the manufacturing efficiencies result in streamlined processes, reduced floor space required for processing, reduced time in manufacture, and also reduced waste by eliminating the potential for defects inherent to processes that utilize welds or bonds to join materials together. It should also be recognized that a more reliable product is produced in that the fastener 10 is fabricated as a single piece of material without incorporating weld joints to maintain its integrity.

Upon forming the fastener 10 to its finished geometry, the fastener 10 is preferably subjected to a passivating process to remove any impurities from the surfaces of the fastener. The passivation may be achieved by electropolishing, chemical passivation, or a hybrid technique known as selective abstraction passivation. The electro-polishing passivation process utilizes a reducing acid environment in conjunction with a source of DC power. The electropolishing process removes impurities from the surfaces of the fastener 10 to a depth of about 20-30 angstroms, depending on the exposure time of the fastener 10 to the reducing acid environment and DC power. The chemical passivation process can be performed in a variety of manners, for example, pickling, wherein the fastener 10 is immersed in a solution of hydrofluoric acid (HF) and nitric acid (HNO3) for a period of time; chelant passivation (citric acid), and selective abstraction, wherein a specifically formulated abstraction chemistry is used in conjunction with electrolysis. The selective abstraction technique removes only the readily soluble passive film contaminants such as iron, nickel, aluminum (grinding residue), and the like. Upon passivating the outer surfaces of the fastener material, desirably the fastener 10 is cleaned utilizing a plasma cleaning process.

The plasma cleaning process removes all foreign materials remaining on the outer surfaces of the fastener material. Some of the plasma cleaning mechanisms that may be used include, for example, induction coupled barrel reactors and capacitance coupled parallel plate reactors.

Upon cleaning the surfaces of the fastener 10, preferably the surfaces are at least partially coated with a bio-adhesive material to facilitate forming a cohesive bond between the fastener 10, the tubular duct 12 and the vessel 16. The bio-adhesive materials may include by-products of the patients own blood, for example, platelet gel formed from the patient's blood. Otherwise, biocompatible adhesives including calcium, for example and without limitation, may be used. These same bio-adhesives may also be introduced while attaching the fastener 10 to the tubular duct 12 and the vessel 16, as discussed in more detail hereafter. Upon coating the fastener 10 with the bio-adhesive, the fastener 10 is generally ready for use. In use, the fastener 10 is deployed by an apparatus, referred to hereafter as a deployment tool 48.

As shown in FIGS. 5-14, the deployment tool 48 has a housing 50, plunger 52 (FIG. 4) and a mandrel 54. The housing 50 has a generally cylindrical sidewall that includes an inner wall 56 and an outer wall 58 spaced radially outwardly from the inner wall 56 and a generally annular base 60. As best shown in FIGS. 6-17, the inner wall 56, outer wall 58 and base 60 define at least in part a hollow chamber 62. Generally opposite the base 60, an annular flange 64 extends radially outwardly from an upper surface 66 of the housing 50. The inner wall 56 has an outer surface 68 defining a generally cylindrical passage 70 projecting axially sufficiently to encircle both the first and second sets of fingers 24, 26 in use, as discussed in more detail hereafter. Desirably, the cylindrical passage 70 terminates at a chamfered surface 72 extending radially outwardly from the cylindrical passage adjacent the flange 64 to facilitate inserting the plunger 52 within the passage 70, as discussed in more detail hereafter. The base 60 has a vacuum channel 74 extending into and communicating with the chamber 62. Desirably, the vacuum channel 74 extends circumferentially about the base 60, or at least extends about a majority of the circumference of the base 60. It should be recognized that the vacuum channel 74 may be constructed having intermittent, circumferentially spaced channels, thereby providing a discontinuous series of vacuum channels (not shown). The vacuum channel 74 is represented as being generally L-shaped in cross section such that the vacuum channel 74 has an enlarged or widened portion 76 adjacent an end 78 of the housing 50. The vacuum channel 74 facilitates maintaining the housing 50 in mating contact with the vessel 16 during the fastening process.

Figure 5:
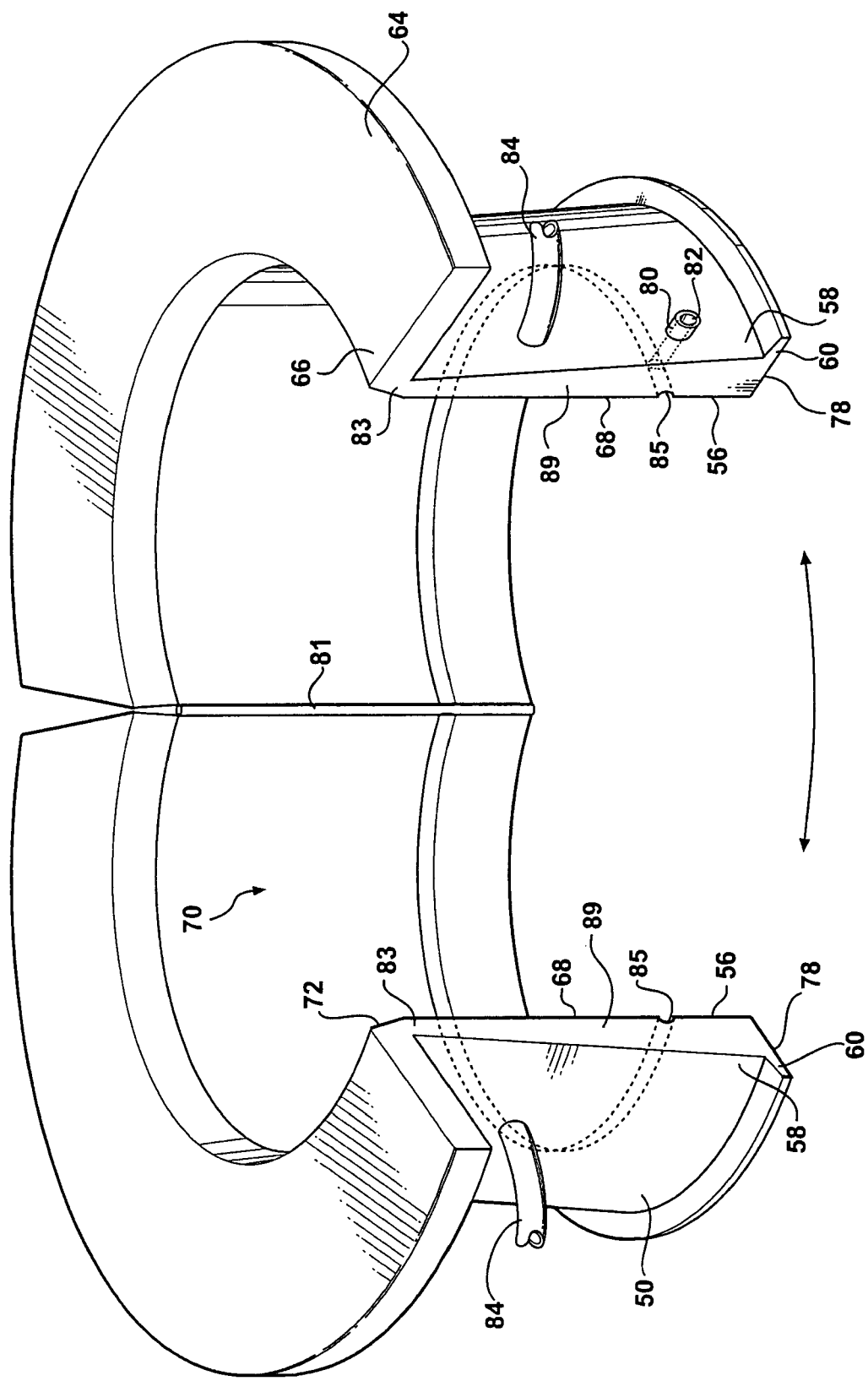
FIG. 5 is a perspective view of one embodiment of a housing used at least in part for deploying the apparatus with the housing shown in an open position.
Figure 5A:
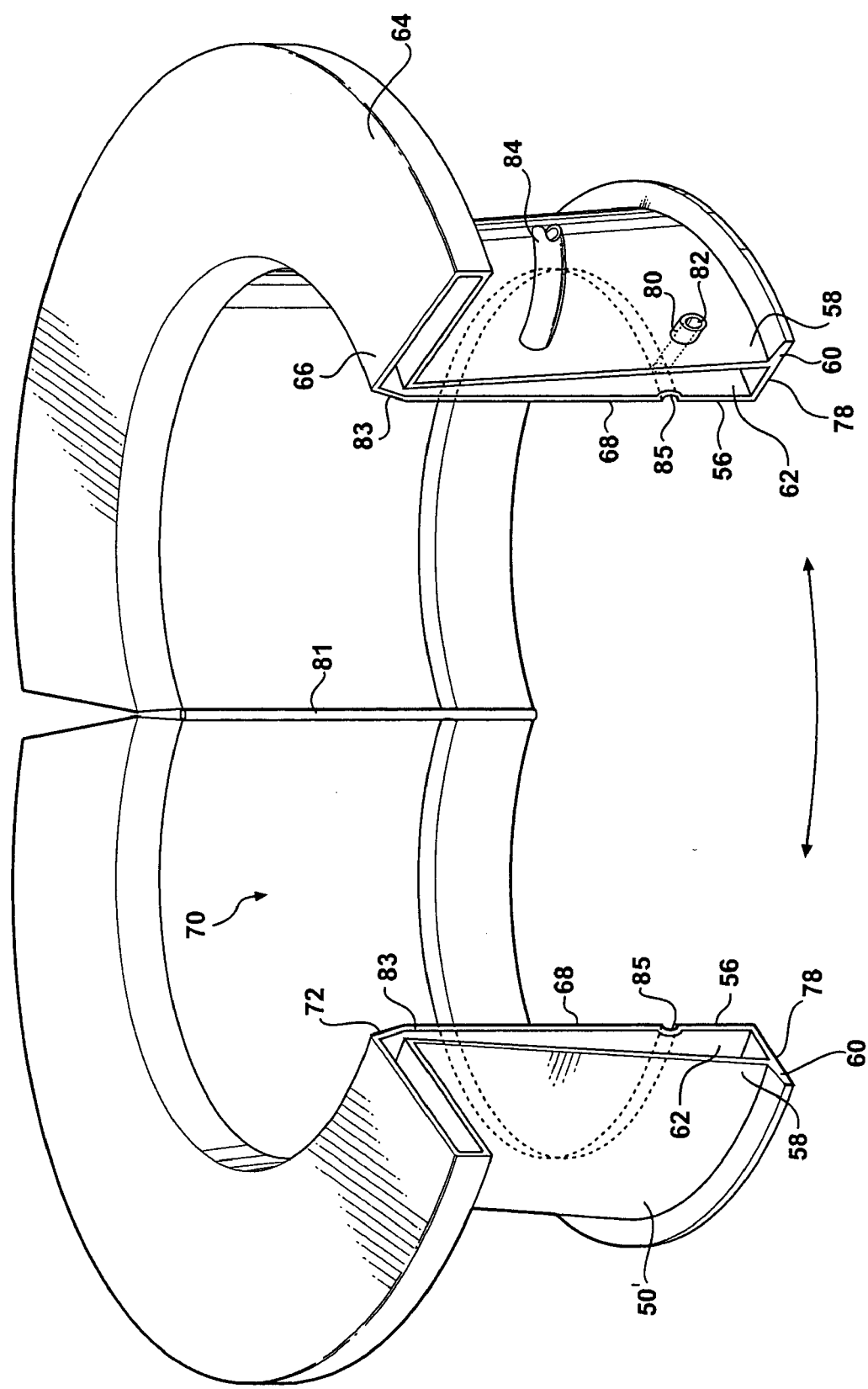
FIG. 5A is a perspective view of another embodiment of a housing used at least in part for deploying the apparatus with the housing shown in an open position.

As shown in FIG. 5, to facilitate placing the housing 50 on the tubular duct 12, and removing the housing 50 from the tubular duct 12, preferably the housing has a hinge 81 along one side of the housing 50 to allow the housing 50 to be opened in a clam-like fashion. The side of the housing 50 generally opposite the hinge 81 has a separable spit 83 allowing halves of the housing 50 to be pivoted about the hinge 81. The chamber 62 is shown having separate and individual halves in each half of the housing 50 wherein each half is separated from the other at the hinge 81 and a pair of partition walls 89. It should be recognized that a housing 50', as shown in FIG. 5A in an alternate embodiment (similar reference numerals are used as in the previous embodiment to describe like features), can incorporate a chamber 62 that is generally continuous throughout the circumference of the housing 50' by eliminating the partition walls 89 from the housing 50 in the previous embodiment. It should also be understood that a suitable air-tight seal is established between the mating halves along the separable split 83 of the housing 50' to prevent a vacuum air leak from resulting along the split 83. The seal may be formed as a result of precise mating engagement between the walls 56, 58 of the two halves along the seam 83, or a separate seal, for example a rubber or polymeric seal (not shown), may be incorporated along the seam 83. It should also be recognized that the hinge 81 may be a mechanical hinge, living hinge, dovetail mechanism allowing complete separation of separate halves of the housing 50, 50', or any other pivot or separation mechanism allowing the housing 50, 50' to be opened along a portion of the walls 56, 58.

Desirably, the housing 50, 50' has an injector conduit 80 extending between the inner and outer walls 56, 58 and passing through the chamber 62. The injector conduit 80 defines a passage 82 separate from the chamber 62 and communicating with the cylindrical passage 70 defined by the inner wall 56 for injecting a bio-adhesive into the passage 70. To facilitate distributing the bio-adhesive uniformly on the fastener 10, preferably the housing 50, 50' has an annular groove 85 formed in the inner wall 56 (FIG. 5).

The housing 50, 50' has a vacuum conduit 84, shown as a pair of vacuum conduits 84 for the housing 50, and as a single vacuum conduit 84 for the housing 50', as shown in FIGS. 5 and 5A, respectively, extending through the outer wall 58 and communicating with the chamber 62. A vacuum pump (not shown) can be connected to the vacuum conduit 84 to draw a vacuum within the chamber 62, thereby creating suction through the vacuum channel 74 in the base 60. Accordingly, upon drawing a vacuum, the suction through the vacuum channel 74 maintains the wall 14 of the vessel 16 firmly against the end 78 of the housing 50, 50' until the vacuum is turned off, as discussed in more detail hereafter. It should be recognized that the housings 50, 50' function similarly to one another, and therefore, for the sake of limiting the discussion, the discussion hereafter references housing 50, but is equally pertaining to the housing 50'.

The mandrel 54 of the deployment tool 48 has a body 86 defining a generally hollowed chamber 87 that is defined at least in part by a generally cylindrical wall 88. The wall 88 is sized for accommodation within the cylindrical passage 70 of the housing 50, and also to accommodate the plunger 52 and the fastener 10 in a biased, linear configuration between an outer surface 90 of the wall 88 and the outer surface 68 defined by the inner wall 56 of the housing 50. The wall 88 preferably has an upper free end 92 with an annular seat 94 extending generally transversely from the wall 88 in an axially spaced or recessed relation to the free end 92. The seat 94 extends laterally from the wall 88 a sufficient distance to accommodate a thickness (t) of the wall 11 of the tubular duct 12, as best shown in FIGS. 10-13, and can be sized to accommodate a range of tubular duct thicknesses, depending on the nature of the surgical procedure being performed. The seat 94 desirably has a vacuum channel 96 extending therethrough and in communication with the chamber 87 and is generally shaped similarly to the vacuum channel 74 in the base 60 of the housing 50. The vacuum channel 96 preferably has a widened portion 98 formed in an upper surface 100 of the seat 94. The widened portion 98 facilitates maintaining the tubular duct 12 in mating contact with the seat 94 while deploying the fastener 10 into the tubular duct 12. Desirably, a locating plug 102 extends axially upwardly from the upper surface 100 of the seat 94. The locating plug 102 is generally concentric with the wall 88 such that an outer surface 104 of the locating plug 102 defines at least in part an annular channel 106 (FIGS. 6-13) between the outer surface 104 and a portion of the wall 88 extending upwardly from the seat 94 to the free end 92. The locating plug 102 is generally conical in shape and has an outer diameter defined by the outer surface 104 and sized to receive and fit within a passage 105 of the tubular duct 12, as best shown in FIGS. 9-13.

Desirably, the locating plug 102 is generally hollow to define at least a portion of the chamber 87, wherein the hollow portion is defined by a wall 108 extending axially from the seat 94. The wall 108 desirably extends generally perpendicularly from the seat 94 for at least a short distance to define a generally cylindrical portion 110 of the locating plug 102 adjacent the seat 94. The cylindrical portion 110 preferably has a vacuum channel 112 in communication with the chamber 87, wherein the vacuum channel 112 is generally shaped similarly as the vacuum channels 74, 96. The vacuum channel 112 desirably has a widened portion 113 extending into the outer surface 104 of the wall 108 to facilitate maintaining the tubular duct 12 in mating contact with the locating plug 102 while deploying the fastener 10 into the tubular duct 10. The vacuum channels 112 are preferably intermittently and equally spaced around the circumference of the cylindrical portion 110 to uniformly maintain the tubular duct 12 abutted against the outer surface 104 while deploying the fastener 10 into the tubular duct 12. It should be recognized that any number of vacuum channels 112 may be incorporated about the circumference of the cylindrical portion 110, and that additional vacuum channels or ports may be formed throughout the locating plug 102, as desired.

The generally cylindrical wall 88 of the mandrel 54 transitions at another end 114 into a generally tapered wall 116 extending from the generally cylindrical wall 88 radially inwardly toward a longitudinal axis 118 of the mandrel 54. The tapered wall 116 converges to a neck-down and generally cylindrical suction nozzle 120. The suction nozzle 120 is sized for operable connection to a vacuum pump (not shown) to create a vacuum within the mandrel 54. Upon creating suction through the suction nozzle 120, a vacuum is created in the chamber 87 defined at least in part by the tapered wall 116, generally cylindrical wall 88, seat 94 and locating plug 102. Accordingly, a suction force is generated through the vacuum channels 96, 112 to maintain the tubular duct 12 engaged with the seat 94 and the outer surface 104 of the locating plug 102 to facilitate attachment of the fastener 10 to the tubular duct 12.

Figure 4:
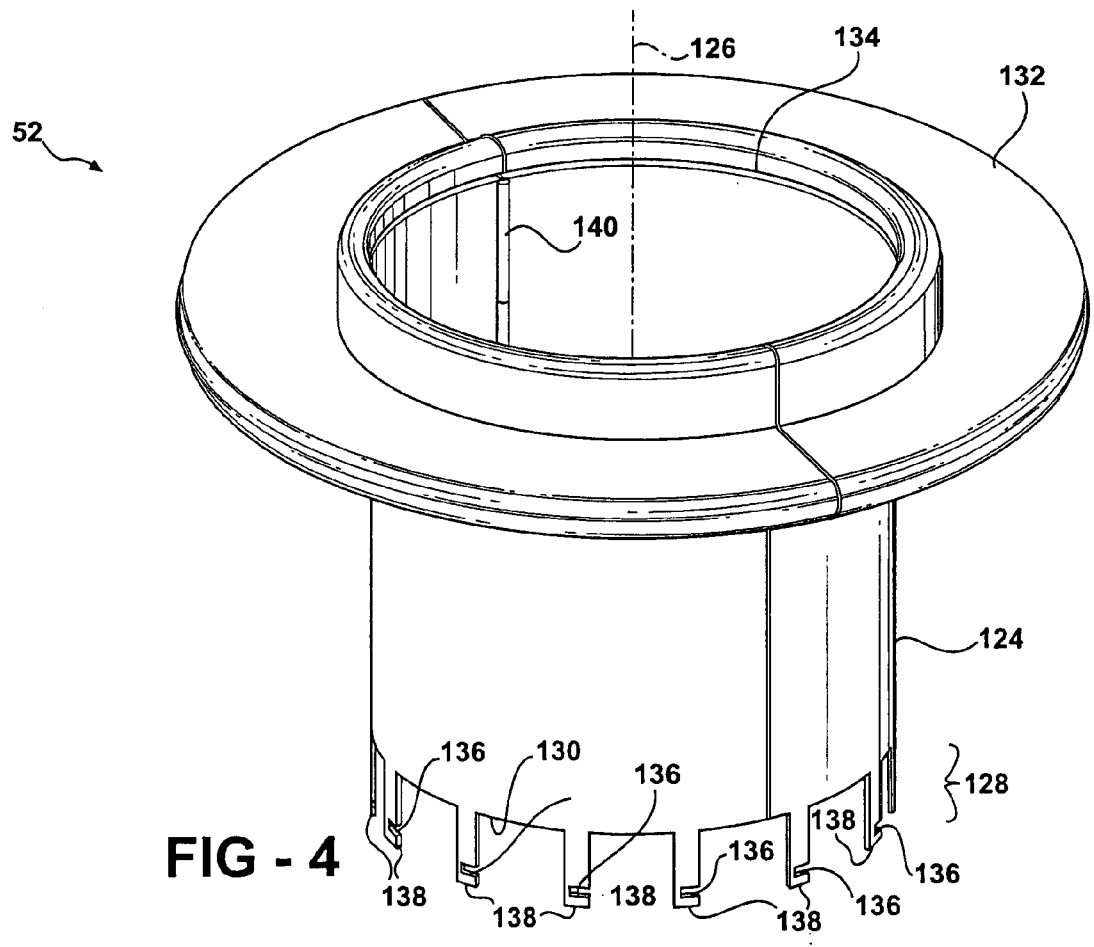
FIG. 4 is a perspective view of a plunger used at least in part for deploying the apparatus.

As best shown in FIG. 4, the plunger 52 has a generally cylindrical wall 124 defining a longitudinal axis 126 and having a plurality of deployment legs 128 extending axially from an end 130 of the wall 124. The plunger 52 has a deployment ring 132 adjacent another end 134 of the wall 124. The deployment ring 132 facilitates insertion of the plunger 52 within the housing 50 by providing a user with an ability to grasp the ring 132 and push the legs 128 into the passage 70 of the housing 50, and also facilitates moving the plunger 52 relative to the housing 50 by allowing the user to pull on the ring 132 to deploy the fastener 10 in the vessel 16.

Each deployment leg 128 preferably has a notch 136 extending generally laterally therein adjacent a free end 138 of each deployment leg 128. The notches 136 face the same general circumferential direction and are sized to receive the tangs 28 extending laterally outwardly from the fastener 10 by rotating the plunger 52 about its longitudinal axis 126 to engage the tangs 28 in the notches 136. Upon registering the tangs 28 in the notches 136, the fastener 10 may be moved axially relative to the housing 50 and the mandrel 54 by pulling and pushing the plunger 52 to facilitate deploying the fastener 10 into the tubular duct 12 and vessel 16, respectively.

The plunger 52 can be opened along its axial length, and desirably has a hinge 140 along a portion of the wall 124. The hinge 140 allows the plunger 52 to separate along at least a portion of the wall 124 to facilitate removal of the plunger 52 from the tubular duct 12 upon deploying the fastener within the vessel 16. It should be recognized that the hinge 140 may be a mechanical hinge, living hinge, dovetail mechanism allowing complete separation of separate halves of the plunger 52, or any other mechanism allowing the plunger 52 to be opened along a portion of the wall 124 in a clam-like fashion.

In attaching the tubular duct 12 to the vessel 16, as best shown in FIGS. 6-17, the fastener 10 is loaded into the deployment tool 48, shown here as already having the plunger 52 inserted within the cylindrical passage 70 of the housing 50. It should be recognized that the plunger 52 may be inserted within the housing 50 after loading the fastener 10 within the housing 50, though this method of loading the fastener 10 relative to the plunger 52 is not shown here.

As best shown in FIG. 6, to facilitate loading the fastener 10 in the housing 50, the fastener 10 is arranged in its unbiased configuration generally concentrically with cylindrical passage 70 adjacent the base 60 of the housing 50. The mandrel 54, and particularly the locating plug 102 is then disposed within the generally cylindrical opening 141 (see FIG. 6) defined by the first set of fingers 24 to position the fastener 10 for insertion into the housing 50.

Figure 7A:
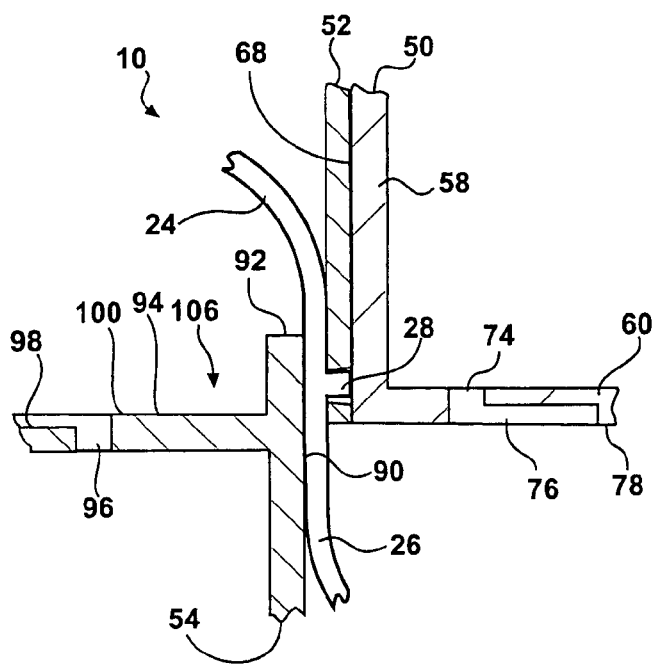
Figure 7:
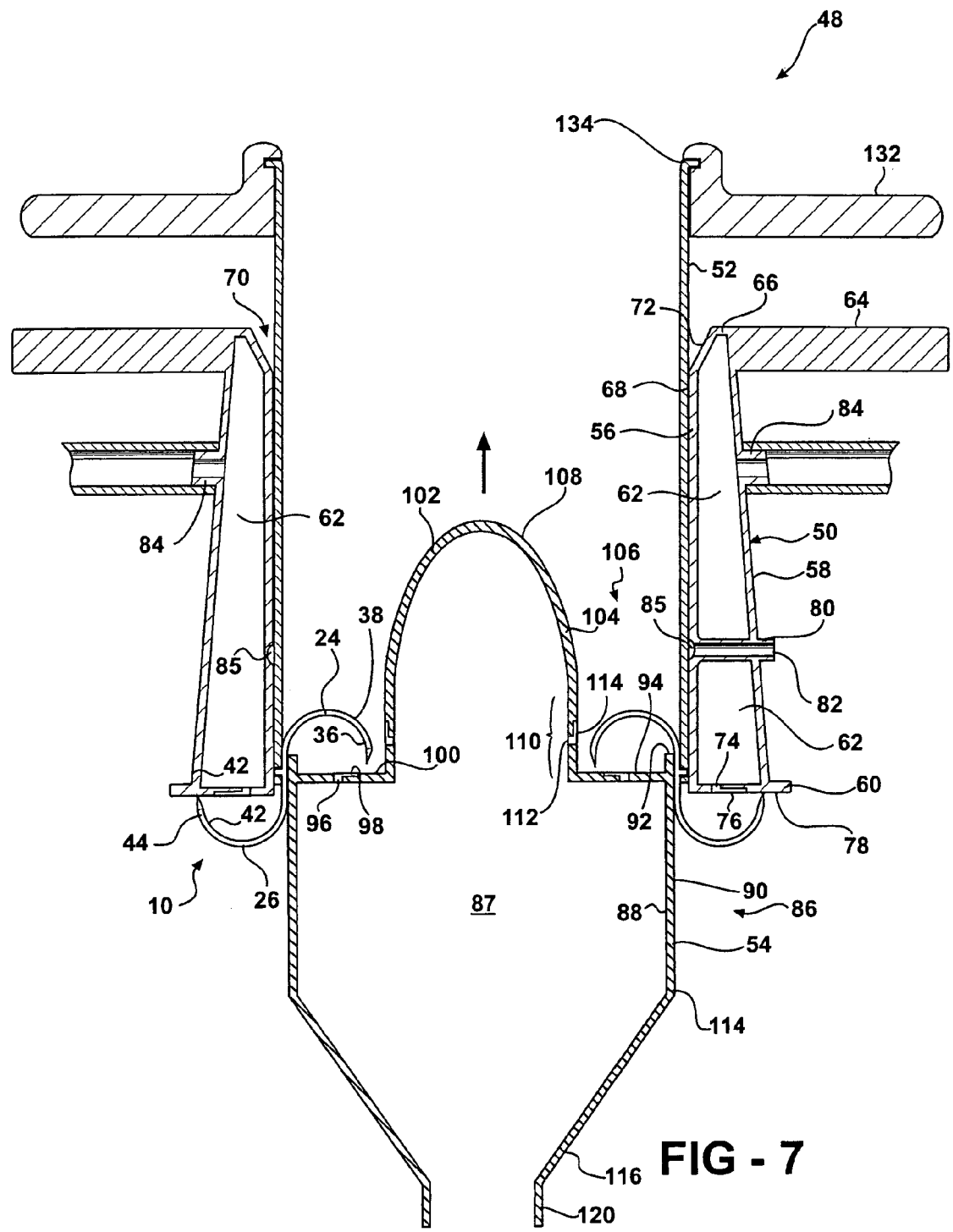

As shown in FIG. 7, the mandrel 54 is moved axially relative to the housing 50 and the plunger 52 to further load the fastener 10 into the housing 50 and plunger 52. As the mandrel 54 moves axially into the housing 50 and plunger 52, the tangs 28 on the fastener 10 are preferably received in the notches 136 of the deployment legs 128 (see FIGS. 6A and 7A). If the tangs 28 do not fully register within the notches 136, the plunger 52 may be rotated about its longitudinal axis 126 to engage the notches 136 with the tangs 28.

Figure 8:
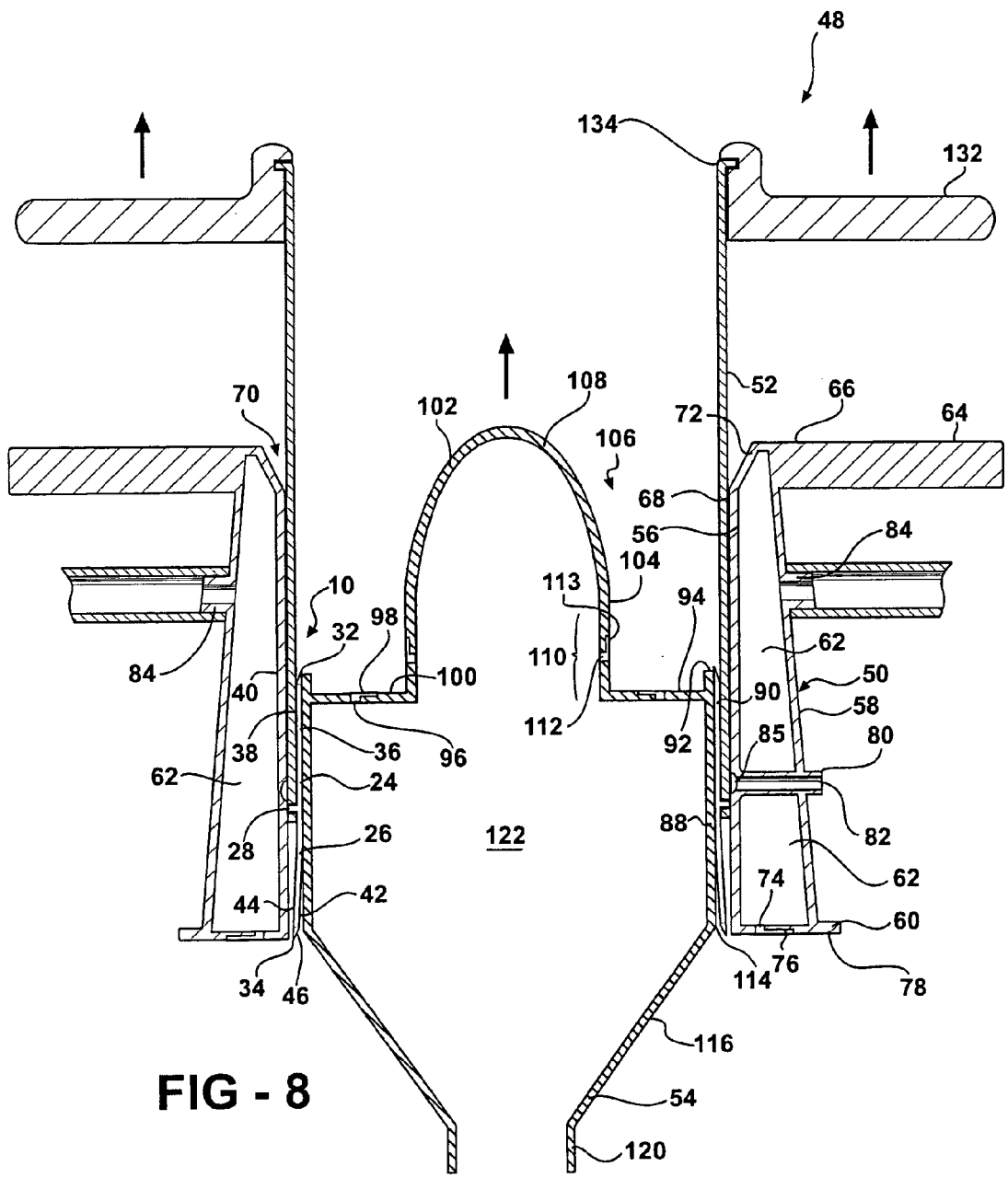

As shown in FIG. 8, the mandrel 54 is further installed axially within the housing 50 and plunger 52 until the end 114 of the cylindrical wall 88 of the mandrel 54 is coplanar or nearly aligned with the end 78 of the housing 50. Additionally, the plunger 52 is moved axially and in the same direction of the mandrel 54 so that the first and second sets of fingers 24, 26 are fully received within the housing 50, and so that the free ends 34 of the second set of fingers 26 are generally coplanar and aligned with the end 114 of the mandrel 54 and the end 78 of the housing 50. It should be recognized that the axial movement of the plunger 52 causes conjoint axial movement of the fastener 10 via engagement of the tangs 28 with the notches 136 in the deployment legs 128. Accordingly, the fastener 10 has its first and second sets of fingers 24, 26 arranged in a biased, linear configuration between the outer surface 90 of the cylindrical wall 88 of the mandrel 54 and the outer surface 68 of the inner wall 56 of the housing 50. Accordingly, it should be understood that outer surface 90 of the mandrel 54 projects axially sufficiently to bear against both the first and second sets of fingers 24, 26 to maintain the fingers 24, 26 in their biased, linear configuration.

Figure 9:
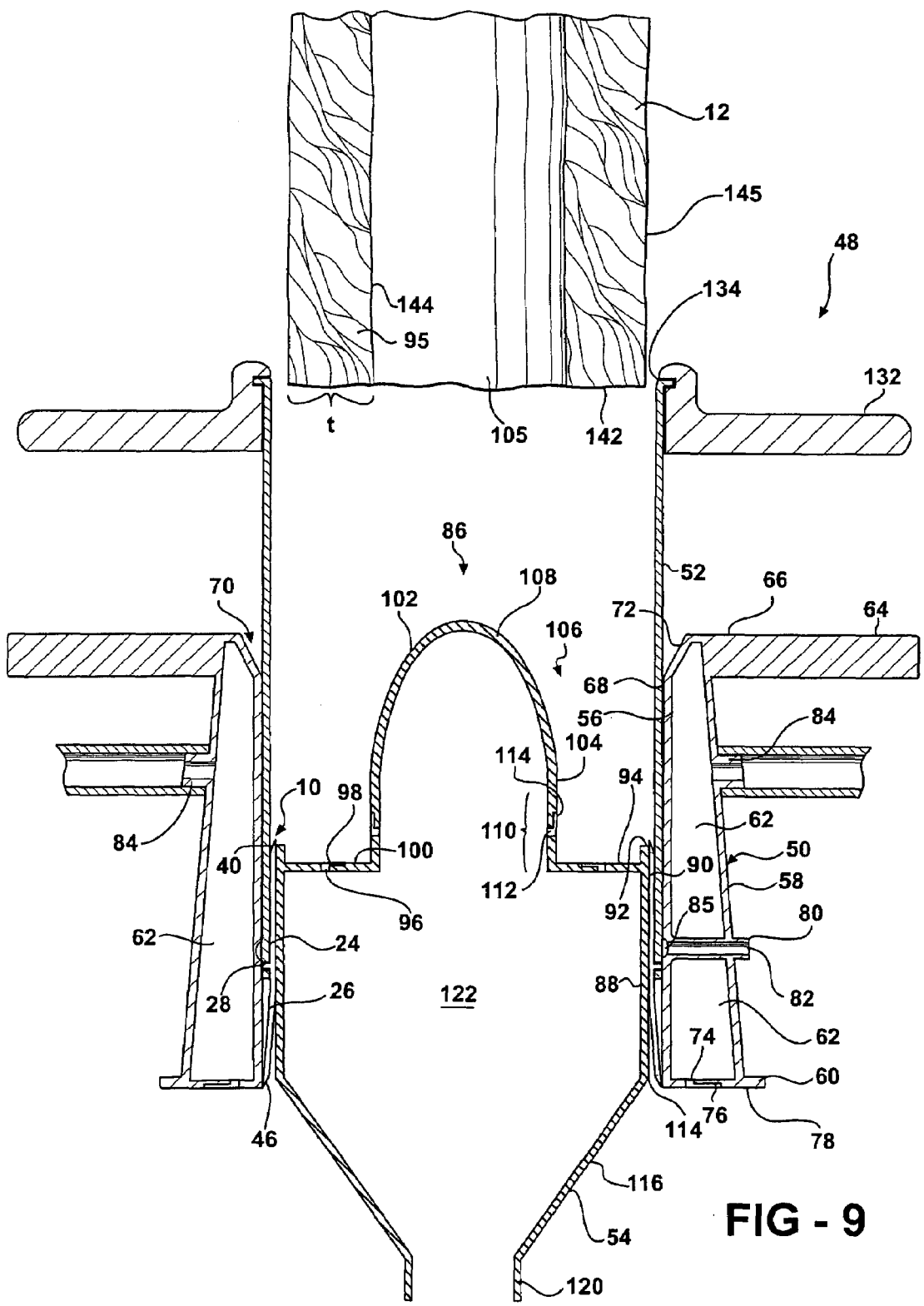
FIGS. 9-14 are cross-sectional views of the apparatus being deployed into the tubular duct.

With the fastener 10 fully loaded within the deployment tool 48, and prior to introducing the tubular duct 12, preferably a bio-adhesive, similar to that used to coat the fastener 10, is injected through the injector conduit 80 so that the bio-adhesive is generally uniformly distributed over the circumference of the fastener 10, and particularly the first and second sets of fingers 24, 26. Upon distributing the bio-adhesive over the circumference of the fastener 10, the tubular duct 12 can be positioned for receipt within the deployment tool 48, as shown in FIG. 9.

Figure 10:
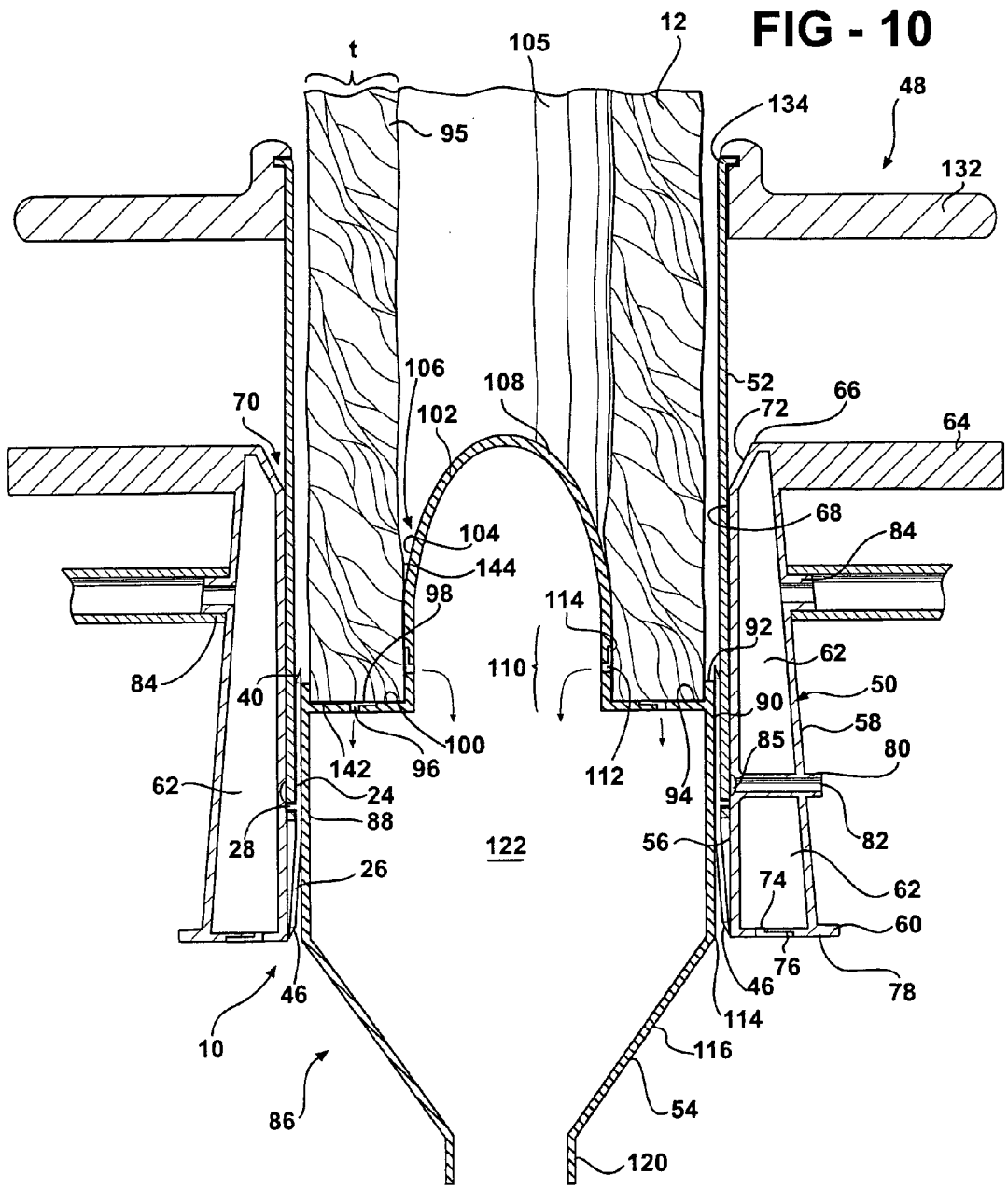
Figure 11:
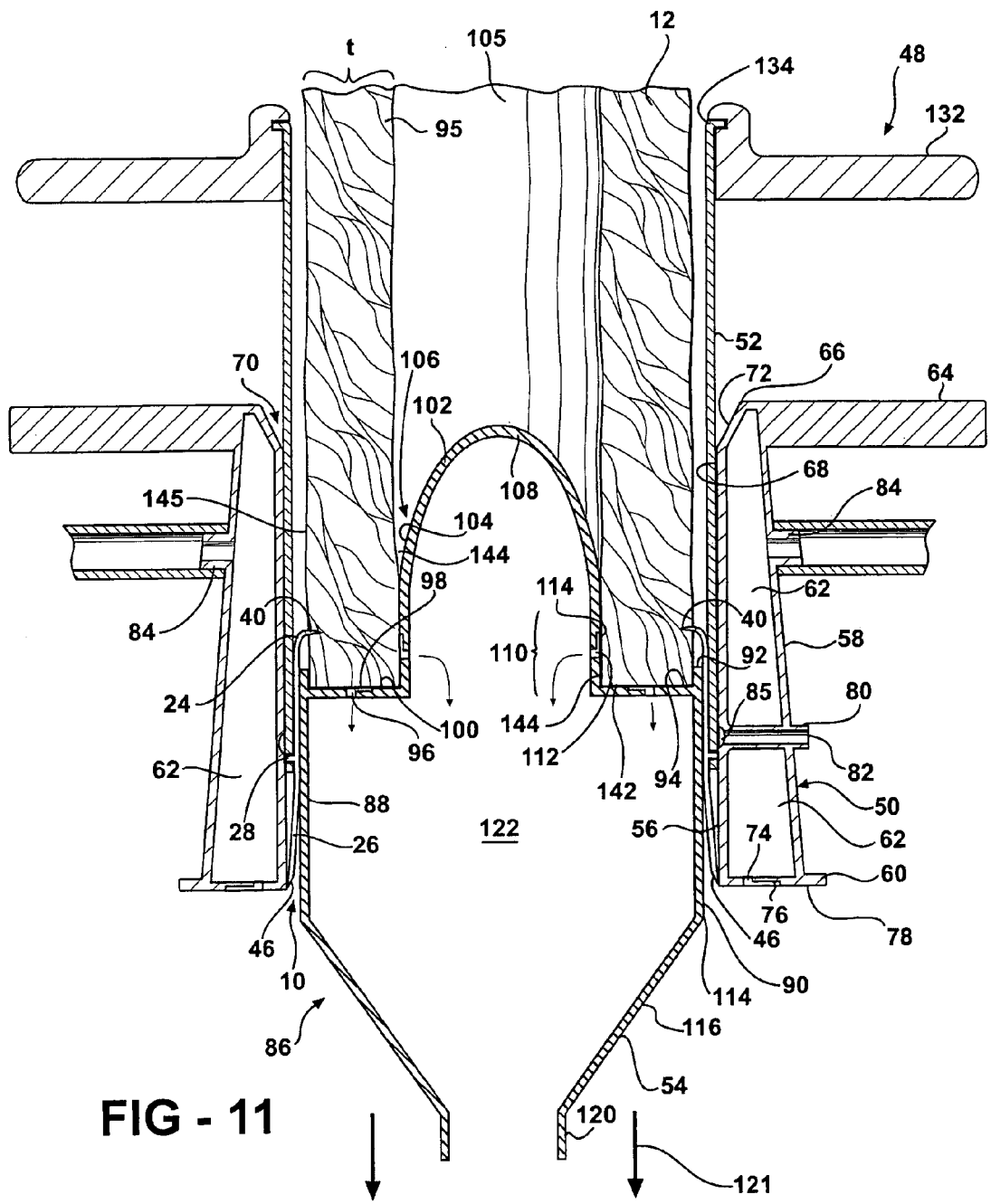
Figure 12:
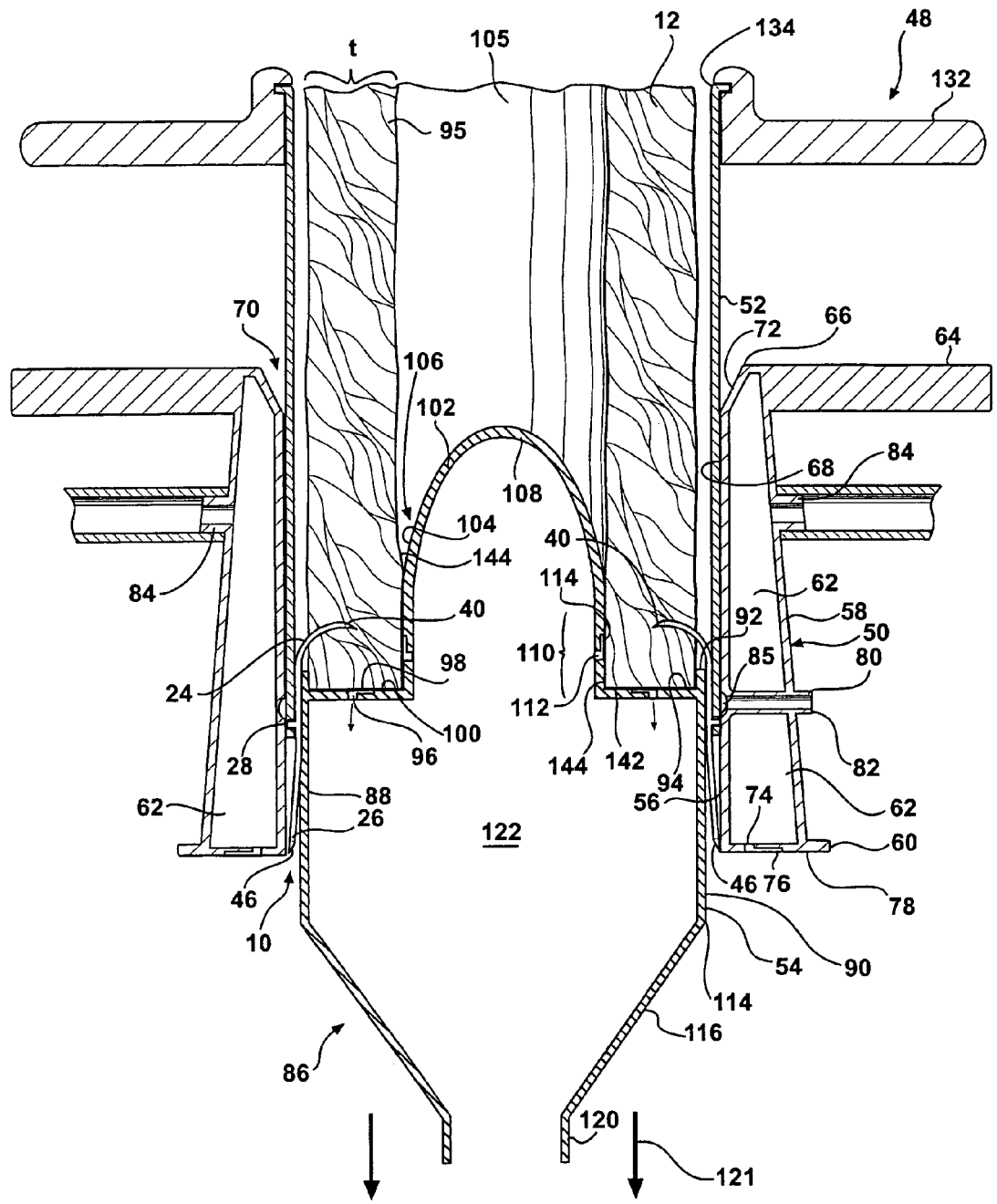

As shown in FIG. 10, the tubular duct 12 is moved axially into the plunger 52 and the housing 50 until an end 142 of the tubular duct 12 having the wall thickness (t) abuts the seat 94 of the mandrel 54. Desirably, the end 142 of the tubular duct 12 fits snugly against the seat 94 and at least a portion of an inner surface 144 of the tubular duct 12 abuts the cylindrical portion 110 of the mandrel 54.

The vacuum source communicating with the suction nozzle 120 is then turned on to create the vacuum within the chamber 87 of the mandrel 54, thereby creating suction within the ports 96, 112 of the mandrel 54. Accordingly, the end 142 of the tubular duct 12 is firmly abutted and maintained against the seat 94, while the inner surface 144 of the tubular duct 12 is firmly abutted and maintained against the cylindrical portion 110 of the locating plug 102.

As shown in FIGS. 11-14, with the tubular duct 12 fully received within the deployment tool 48, the mandrel 54 is moved axially away from the housing 50 and plunger 52 (in the direction of the arrows 121). The tubular duct 12 remains in abutting contact with the seat 94 and the cylindrical portion 110 as a result of the suction through the ports 96, 112, and thus, the tubular duct 12 moves with the mandrel 54 relative to the housing 50 and plunger 52. Accordingly, as the mandrel 54 and tubular duct 12 move axially, the first set of fingers 24 begin to clear the free end 92 of the cylindrical wall 88, thereby removing the bias from the first set of fingers 24 and allowing them to return to their unbiased, generally hook shaped configuration. As the first set of fingers 24 move toward their unbiased, generally hook shaped configuration, they curl radially inwardly toward the longitudinal axis 20 of the fastener 10, and in so doing, pierce an outer surface 145 of the tubular duct 12 (see FIG. 11) and thereby attach themselves to the wall 11 of the tubular duct 12. Desirably, the fingers 24 do not pierce the inner surface 144 of the wall 11 to avoid interfering with fluid flow in the tubular duct 12.

Figure 13:
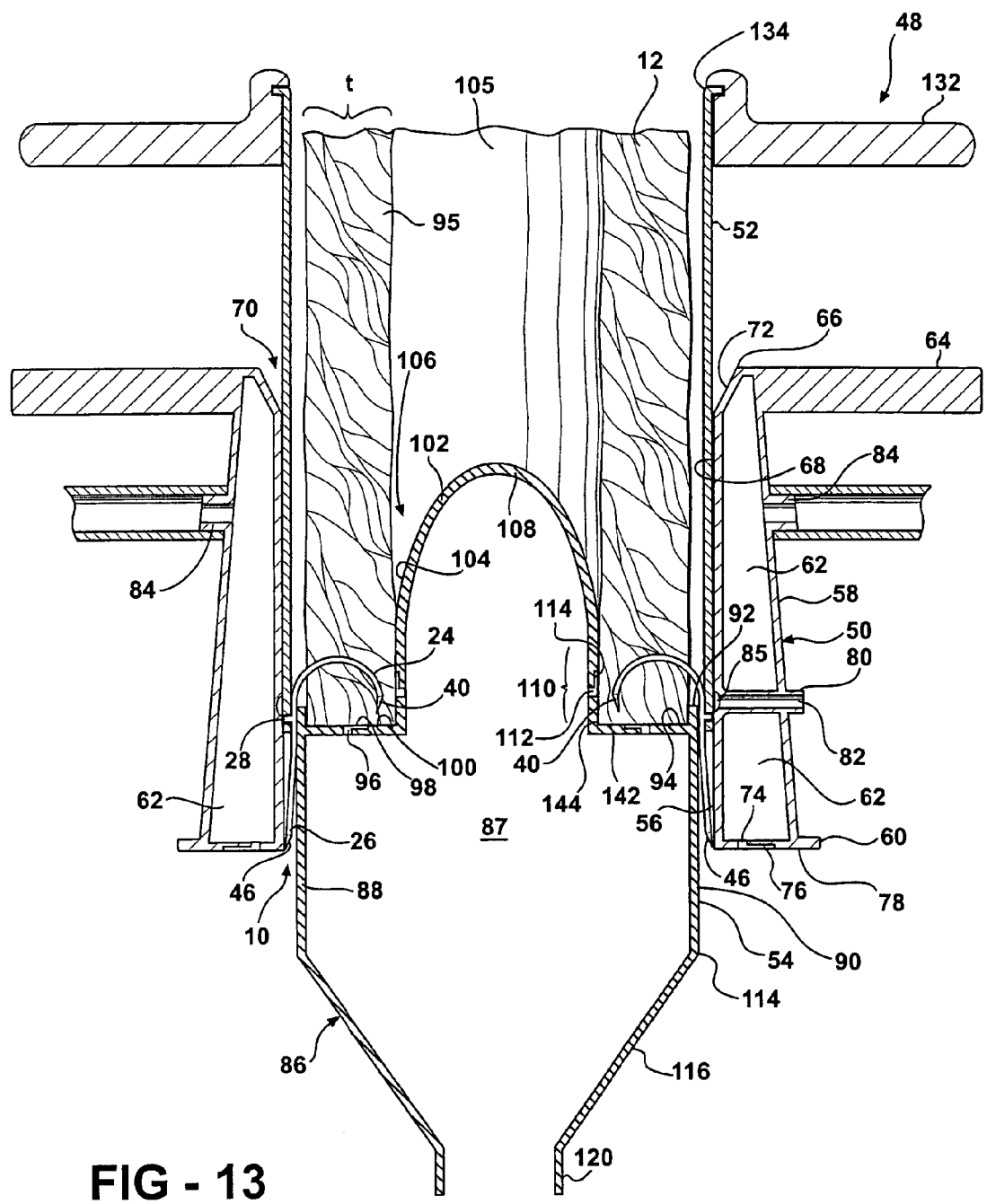

As the first set of fingers 24 engage the tubular duct 12, desirably, the bevels 40 in the first set of fingers 24 facilitate movement of the first set of fingers 24 toward their unbiased, generally arcuate configuration. It should be recognized that the configuration of the bevels 40 facilitates the return of the first set of fingers 24 to their unbiased, arcuate configuration by deflecting the fingers 24 against the tissue of the tubular duct 12 toward their unbiased, generally hook shaped configuration. The mandrel 54 and the tubular duct 12 continue to move axially relative to the housing 50 and plunger 52 until the first set of fingers are fully engaged with the tubular duct 12, as shown in FIG. 13.

Figure 14:
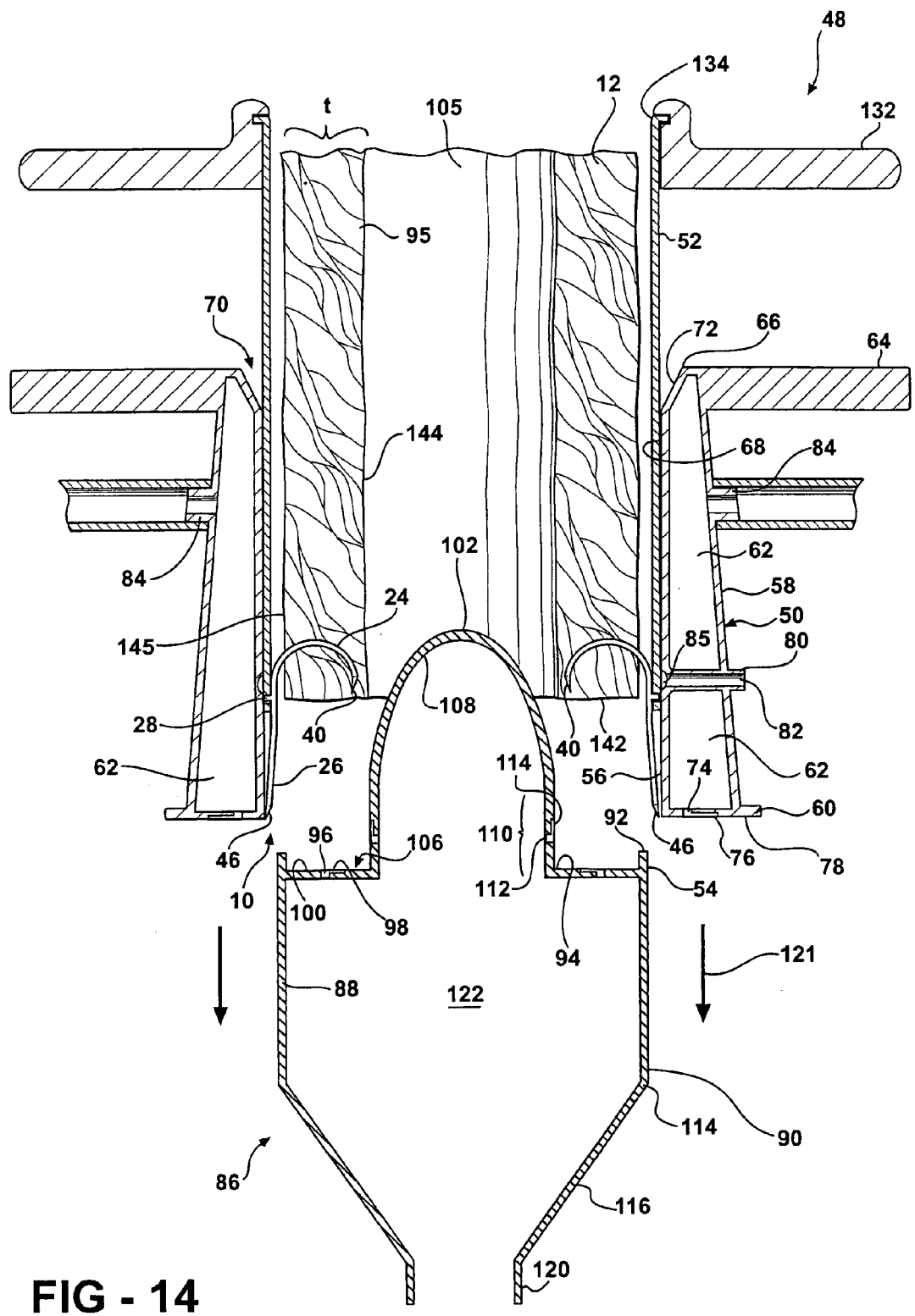

Upon full engagement of the first set of fingers 24 with the tubular duct 12, the vacuum source connected to the suction nozzle 120 is turned off, thereby eliminating the vacuum within the chamber 87 and eliminating the suction at the ports 96, 112. Accordingly, the mandrel 54 can be detached from the tubular duct 12 and removed from the housing 50, as shown in FIG. 14.

Figure 15:
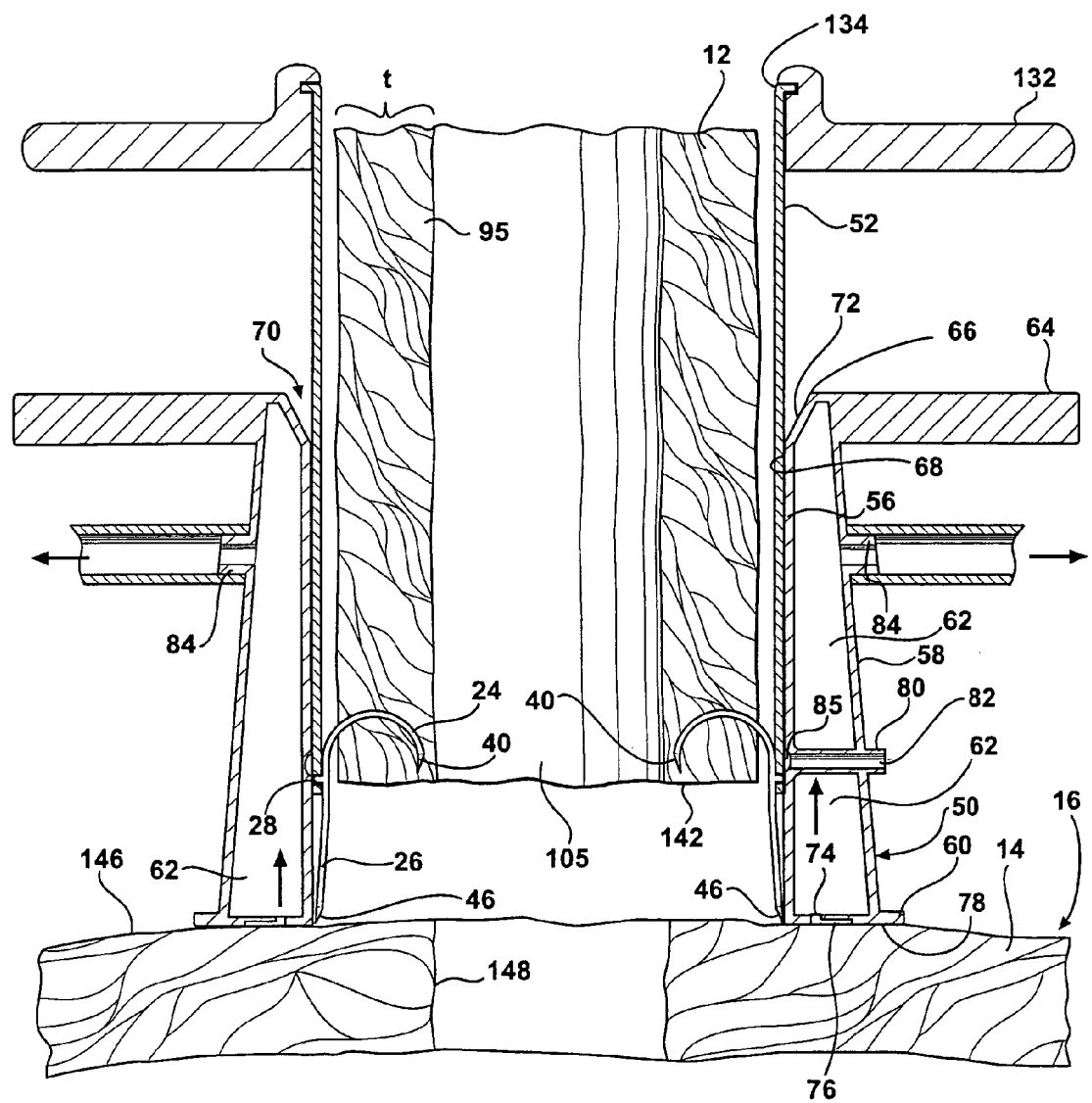
FIGS. 15-17 are cross-sectional views of the apparatus being deployed into the wall of the vessel.

As shown in FIG. 15, to attach the fastener 10 to the wall 14 of the vessel 16, the base 60 of the housing 50 is placed in mating contact with an outer surface 146 of the wall 14. It should be recognized that the wall 14 of the vessel 16 has been prepared by forming an appropriately sized hole or opening 148 through the wall 14 prior to placing the housing 50 in mating contact with the wall 14. It should also be recognized that the cylindrical passage 70 of the housing 50 is desirably positioned concentrically relative to the opening 148 in the wall 14 of the vessel 16. Upon engaging the base 60 with the wall 14, the vacuum source connected to the vacuum conduit 84 is turned on to create a vacuum within the chamber 62 (represented here with arrows), thereby creating suction through the ports 74 in the base 60. Accordingly, the wall 14 of the vessel 16 is maintained in abutting, flush contact against the end 78 of the base 60. As the housing 50 remains in abutting contact with the wall 14 of the vessel 16, the wall 14 is generally free to move while the housing 50 moves conjointly with the wall 14, such as would occur with the pulsation of a heart wall. Accordingly, the heart may function and pulsate normally, and without undue constraint, while the housing 50 is maintained in abutting contact with the heart wall 14 throughout the surgical procedure.

Figure 16:
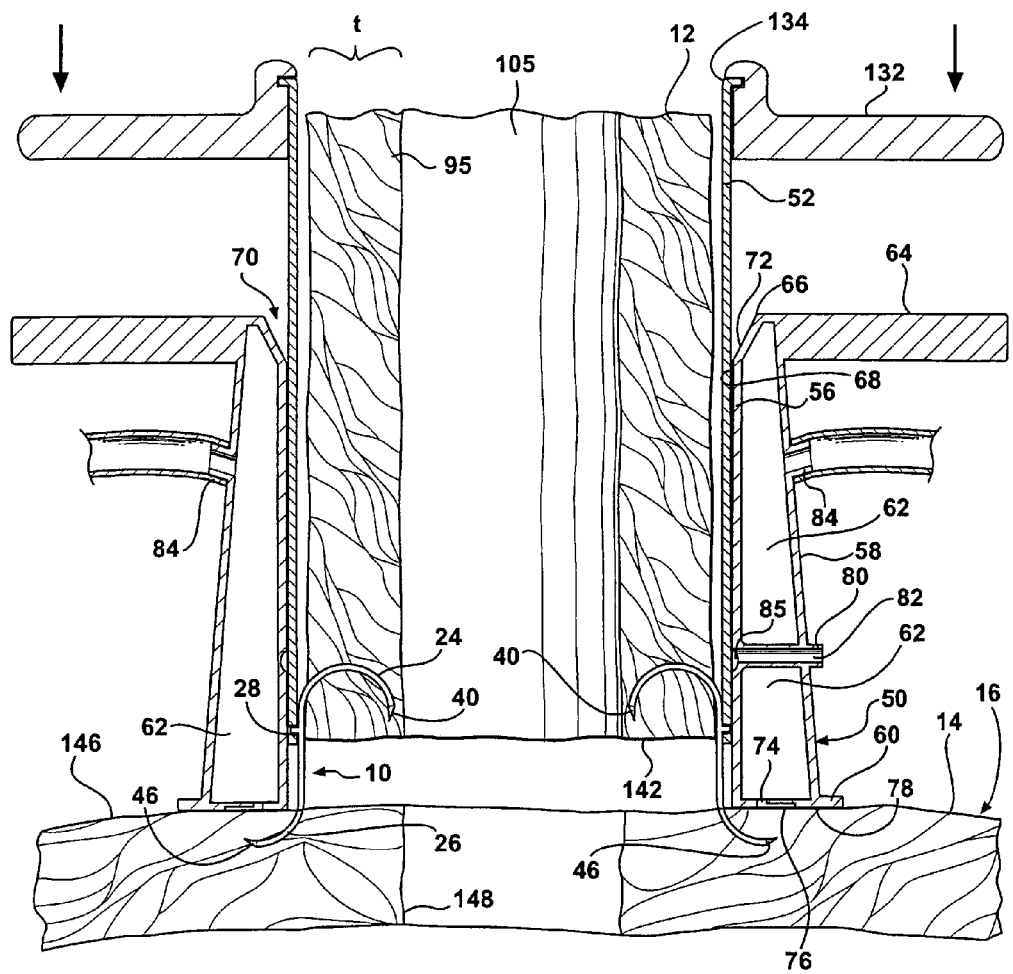

As shown in FIG. 16, the plunger 52 is then moved axially toward the vessel 16 and relative to the housing 50. As the second set of fingers 26 clear the end 78 of the housing 50, the second set of fingers 26 move radially outwardly from the longitudinal axis 20 and toward their unbiased, generally hook shaped configuration. As the free ends 34 of the second set of fingers 26 engage the wall 14 of the vessel 16, the bevels 46 in the second set of fingers 26 facilitate the movement of the second set of fingers 26 toward their unbiased, generally hook shaped configuration in similar fashion as the bevels 40 on the first set of fingers 24. It should be recognized that the bevels 40, 46 are desirably formed on generally opposite sides of their respective fingers 24, 26 in order to facilitate movement of the fingers 24, 26 toward their respective unbiased, generally arcuate configurations.

Figure 17:
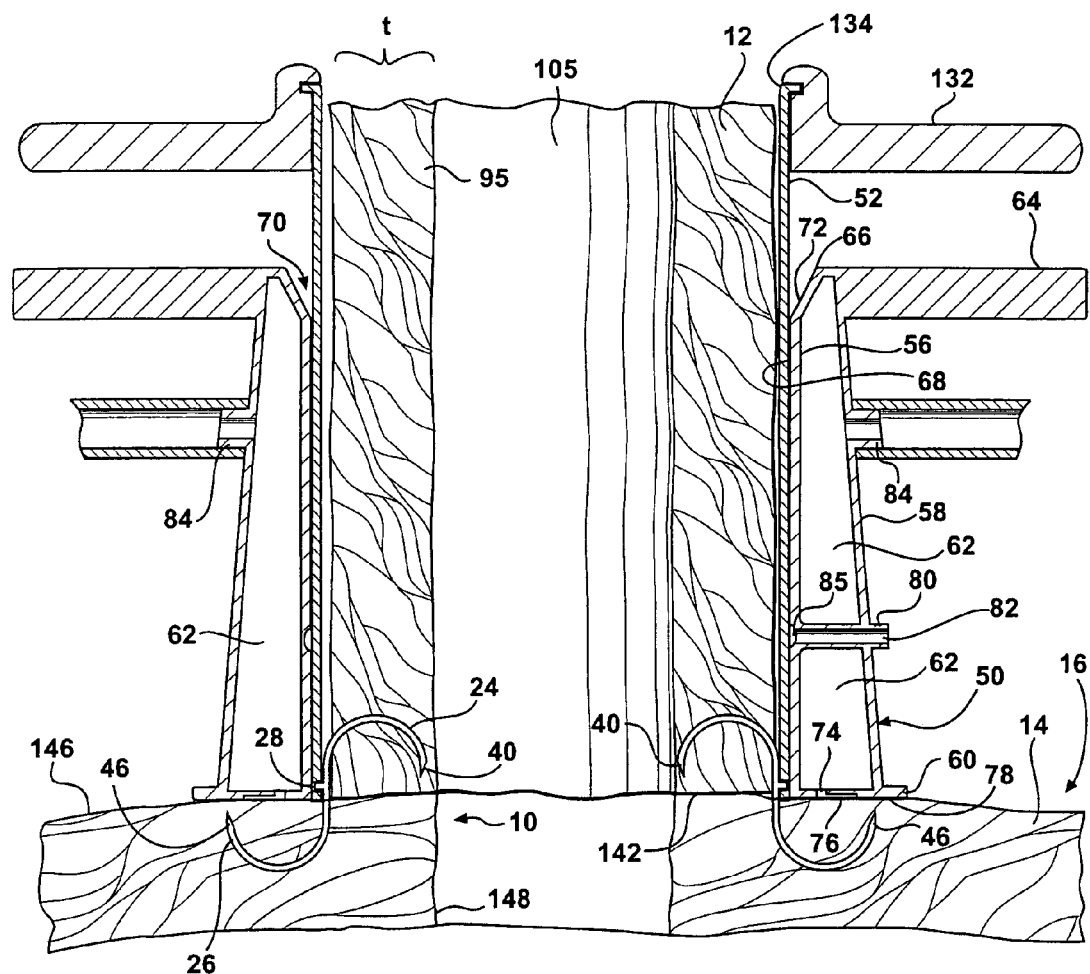

As shown in FIG. 17, when the plunger 52 is moved axially to its fully assembled position, the second set of fingers 26 are fully engaged and fastened in the wall 14 of the vessel 16. It should be recognized that the tubular duct 12 moves conjointly with the plunger 52 as a result of the engagement of the first set of fingers 24 with the tubular duct 12. Thereafter, the plunger 52 may be rotated about its longitudinal axis 126 in a direction generally opposite to that when the plunger was engaged with the tangs 28, thereby disengaging the notches 136 within the deployment legs 128 from the tangs 28. Once the tangs 28 are disengaged from the notches 136, the plunger may be moved axially away from the vessel 16 until it is fully removed from the housing 50. Upon removing the plunger 52 from the housing 50, the plunger 52 may be opened in clam-like fashion by separating opposite halves of the plunger 52 via the hinge 140. The plunger 52 may then be removed from the tubular duct 12.

The vacuum source communicating with the housing 50 is then turned off, thereby removing the vacuum from within the chamber 62 of the housing 50 and eliminating the suction from the ports 74. Accordingly, the housing 50 may be removed from its abutting engagement from the wall 14 of the vessel 16, and removed from the tubular duct 12 by opening the housing 50 about the hinge 81.

It should be recognized that the bio-adhesive both coating the fastener 10 and injected over the circumference of the fastener 10 facilitates forming a bond between the fastener 10, the tubular duct 12 and the vessel 16. It should also be recognized that the tubular duct 12 and vessel 16 form a cohesive biological bond between themselves over time, though the fastener 10 acts to reassure the connection of the tubular duct 12 to the vessel 16. Further, it should be recognized that the fastener 10 desirably imparts a slight biasing force, though nearly in its fully unbiased configuration, tending to draw the wall 11 of the tubular duct 12 toward the wall 14 of the vessel 16, thereby maintaining a leak-proof anastomosis between the tubular duct 12 and the vessel 16.

It is to be understood that the embodiments discussed above are exemplary embodiments of the presently preferred constructions, and thus are intended to be illustrative and not limiting. The scope of the invention is defined by the following claims.

I claim:

1. An apparatus for securing a tubular duct having a wall with an outside surface and a first end to a vessel having a wall with an outside surface, comprising:
an annulus having a longitudinal axis;
a first set of fingers extending at least in part axially from said annulus in one direction, said first set of fingers being movable between first and second configurations, said first set of fingers extending at least in part radially inwardly toward said longitudinal axis while in their second configuration into the outside surface of the wall of the tubular duct;
a second set of fingers extending at least in part axially from said annulus in another direction generally opposite said one direction, said second set of fingers being movable between first and second configurations, said second set of fingers extending at least in part radially outwardly from said longitudinal axis while in their second configuration into the outside surface of the vessel; and
said first set of fingers configured to penetrate the outside surface of the wall of the tubular duct as they move from their first configuration to their second configuration and said second set of fingers configured to penetrate the outside surface of the wall of the vessel as they move from their first configuration to their second configuration;
wherein the first set of fingers moves into the outside surface of the wall of the tubular duct as the first set of fingers moves from their first configuration to their second configuration and wherein the second set of fingers moves into the outside surface of the vessel as the second set of fingers moves from their first configuration to their second configuration.

2. The apparatus of claim 1 wherein each of said first set of fingers have an outer surface facing generally away from said longitudinal axis when in their first configuration.

3. The apparatus of claim 2 wherein each of said outer surfaces extend to a free end and have a bevel extending from said free end along at least a portion of said outer surface.

4. The apparatus of claim 3 wherein said bevels extend from said free ends generally away from said longitudinal axis when in said first configuration.

5. The apparatus of claim 1 wherein each of said second set of fingers have an inner surface facing generally toward said longitudinal axis when in their first 3 configuration.

6. The apparatus of claim 5 wherein each of said inner surfaces extend to a free end and have a bevel extending from said free end along at least a portion of said inner surface.

7. The apparatus of claim 6 wherein said bevels extend from said free ends generally toward said longitudinal axis when in said first configuration.

8. The apparatus of claim 1 wherein said fingers are constructed of resiliently springy material.

9. The apparatus of claim 1 wherein said annulus has a midsection extending annularly generally between said first and said second sets of fingers.

10. The apparatus of claim 9 wherein said midsection is generally zig-zag shaped.

11. The apparatus of claim 9 wherein said midsection has a plurality of tangs extending radially therefrom.

12. The apparatus of claim 1 wherein said first set of fingers or circumferentially offset from said second set of fingers.

13. The apparatus of claim 1 wherein said first and second sets of fingers are generally linear while in their first configurations and nonlinear in while in their second configurations.

14. The apparatus of claim 1 wherein said first and second sets of fingers are at least partially arcuate while in their second configurations.

15. The apparatus of claim 1 wherein said first and second sets of fingers are generally hook shaped white in their second configurations.

16. The apparatus of claim 1 wherein said first and second sets of fingers are generally S-shaped in axial cross section while in their second configuration.

17. An apparatus for securing a tubular duct having a wall with an outside surface and a first end to a vessel having an outer wall with an outside surface, comprising:
 an annulus having a longitudinal axis;
 a first set of fingers extending axially from said annulus in one direction, said first set of fingers being movable between a biased, generally flattened configuration and a unbiased, generally hook shaped configuration, said first set of fingers extending at least in part radially inwardly toward said longitudinal axis while in their unbiased configuration;
 a second set of fingers extending axially from said annulus in a second direction generally opposite said one direction, said second set of fingers being movable between a biased, generally flattened configuration and a unbiased, generally hook shaped configuration, said second set of fingers extending at least in part radially outwardly from said longitudinal axis while in their unbiased configuration;
 a mandrel having an outer surface received in said annulus and said outer surface projecting axially sufficiently to bear against both of said sets of fingers;
 a housing encircling said annulus and projecting axially sufficiently to encircle both of said sets of fingers;
 said mandrel and said housing arranged in one relative position to bias both of said sets of fingers in their generally flattened configuration;
 said mandrel and said housing being moveable axially relative to one another in a selected one of two opposite directions a distance sufficient to relieve the bias applied on a selected set of said fingers and enable said selected set of fingers to move toward their generally hook shaped configuration, and
 the fingers of one of said sets being capable of embedding themselves into said wall of said tubular duct and the fingers of the other of said sets being capable of embedding themselves into said outer wall of said vessel;
 wherein the first set of fingers moves into the outside surface of the wall of the tubular duct as the first set of fingers moves from their biased to their unbiased configuration and wherein the second set of fingers moves into the outside surface of the vessel as the second set of fingers moves from their biased to their unbiased configuration.

18. The apparatus of claim 17 wherein one of said sets of fingers extend radially inwardly toward said longitudinal axis of said annulus while in their generally hook shaped configuration.

19. The apparatus of claim 18 wherein the other of said sets of fingers extend radially outwardly from said longitudinal axis of said annulus while in their generally hook shaped configuration.

20. The apparatus of claim 17 wherein said mandrel has an annular seat for the accommodation of one end of said tubular duct.

21. An apparatus for deploying an annulus to secure a tubular duct having a wall with an outside surface and a first end to a vessel having a wall with an outside surface, the annulus having a longitudinal axis with a first and a second set of fingers with the first set of fingers extending axially from the annulus in one direction and being movable between a biased, generally flattened configuration and a unbiased, generally hook shaped configuration extending generally inwardly toward the longitudinal axis while in their unbiased configuration into the outside surface of the wall of the tubular duct and the second set of fingers extending axially from the annulus in a second direction generally opposite the direction of the first set of fingers and being movable between a biased, generally flattened configuration and a unbiased, generally hook shaped configuration extending generally outwardly from the Longitudinal axis while in their unbiased configuration into the outside surface of the vessel wherein the first set of fingers operate to penetrate an outside surface of the wall of a tubular duct as they move from their biased configuration to their unbiased configuration and the second set of fingers operate to penetrate an outside surface of the wall of the vessel as they move from their biased configuration to their unbiased configuration to attach the tubular duct to the vessel wherein the first set of fingers moves into the outside surface of the wall of the tubular duct as the first set of fingers moves from their first configuration to their second configuration and wherein the second set of fingers moves into the outside surface of the vessel as the second set of fingers moves from their first configuration to their second configuration, said apparatus comprising:
 a housing having an inner wall defining a generally cylindrical passage;
 a generally cylindrical plunger sized for receipt in said cylindrical passage; and
 a mandrel having a generally cylindrical wall projecting axially sufficiently to bear against the first and second sets of fingers and sized to accommodate the annulus and the plunger between said outer surface and said passage of said housing,

22. The apparatus of claim 21 wherein said housing further comprises an outer wall and an annular base connecting said outer wall to said inner wall and defining at least in part a chamber between said inner and outer walls.

23. The apparatus of claim 22 further comprising a conduit passing through said outer wall of said housing and communicating said chamber.

24. The apparatus of claim 22 wherein said base has a port extending into said chamber.

25. The apparatus of claim 24 wherein said port extends circumferentially about said base.

26. The apparatus of claim 22 further comprising a conduit extending between said inner and outer walls of said housing.

27. The apparatus of claim 26 wherein said conduit passes through said chamber.

28. The apparatus of claim 27 wherein said conduit defines a passage separate from said chamber.

29. The apparatus of claim 21 wherein said mandrel has an annular seat extending transversely to said wall, said annular seat and said wall defining at least in part a chamber within said mandrel.

30. The apparatus of claim 29 wherein said annular seat has a port 2 extending into said chamber.

31. The apparatus of claim 30 wherein said port extends circumferentially about said seat.

32. The apparatus of claim 29 wherein a locating plug extends generally transversely from said seat and generally concentrically to said wall.

33. The apparatus of claim 32 wherein said locating plug has a wall with an inner surface defining at least in part said chamber.

34. The apparatus of claim 33 wherein said wall has a port extending therethrough and into said chamber.

35. The apparatus of claim 21 wherein said housing, said plunger and said mandrel are operable to move axially relative to one another.

36. The apparatus of claim 21 wherein said plunger has a wall with a hinge allowing said wall to articulate about said hinge.

37. The apparatus of claim 36 wherein said wall of said plunger is separable along a portion of said wall diametrically opposite said hinge.

38. The apparatus of claim 21 wherein said housing has a wall with a binge allowing said wall to articulate about said hinge.

39. The apparatus of claim 38 wherein said wall of said housing is separable along a portion of said wall diametrically opposite said hinge.

40. An apparatus for securing a tubular duct having a wall with an outside surface and a non-everted first end to a vessel having a wall with an outside surface, comprising:
   an annulus having a longitudinal axis;
   a first set of fingers extending at least in part axially from said annulus in one direction, said first set of fingers being movable between first and second configurations, said first set of fingers extending at least in part radially inwardly toward said longitudinal axis while in their second configuration into the outside surface of the wall of the tubular duct;
   a second set of fingers extending at least in part axially from said annulus in another direction generally opposite said one direction, said second set of fingers being movable between first and second configurations, said second set of fingers extending at least in part radially outwardly from said longitudinal axis while in their second. Configuration into the outside surface of the vessel; and
   said first set of fingers configured to penetrate the outside wall of the tubular duct as they move from their first configuration to their second configuration and said second set of fingers configured to penetrate the outside surface of the wall of the vessel as they move from their first configuration to their second configuration wherein the first set of fingers moves into the outside surface of the wall of the tubular duct as the first set of fingers moves from their first configuration to their second configuration and wherein the second set of fingers moves into the outside surface of the vessel as the second set of fingers moves from their first configuration to their second configuration.

41. A method of securing a tubular duct having a wall with an outside surface and a first end to a vessel having a wall with an outside surface, comprising the steps of:
   (a) providing an apparatus comprising:
      an annulus having a longitudinal axis;
      a first set of fingers extending at least in part axially from said annulus in one direction, said first set of fingers being movable between first and second configurations, said first set of fingers extending at least in part radially inwardly toward said longitudinal axis while in their second configuration;
      a second set of fingers extending at least in part axially from said annulus in another direction generally opposite said one direction, said second set of fingers being movable between first and second configurations, said second set of fingers extending at least in part radially outwardly from said longitudinal axis while in their second configuration; and
      said first set of fingers configured to penetrate the outside wall of the tubular duct as they move from their first configuration to their second configuration and said second set of fingers configured to penetrate the outside surface of the wall of the vessel as they move from their first configuration to their second configuration;
   (b) restraining the first set of fingers in their first configuration;
   (c) restraining the second set of fingers in their first configuration;
   (d) positioning the apparatus in proximity to the tubular duct so that the first set of fingers in their first configuration are disposed around the outside surface of the tubular duct;
   (e) allowing the first set of fingers to move from their first configuration to their second configuration so that the first set of fingers penetrate the outside wall of the tubular duct;
   (f) positioning the apparatus in proximity to the vessel so that the second set of fingers in their first configuration are disposed around the outside surface of the vessel;
   (e) allowing the second set of fingers to move from their first configuration to their second configuration so that the second set of fingers penetrate the outside surface of the wall of the vessel.

* * * * *